US012740928B2

(12) United States Patent
Lourenco et al.

(10) Patent No.: US 12,740,928 B2

(45) Date of Patent: Sep. 22, 2026

(54) SURFACTANT CONTAINING FORMULATION OF PSEUDO-CERAMIDES

(71) Applicant: Symrise AG, Holzminden (DE)

(72) Inventors: Carolina Lourenco, Cotia (BR); Sabine Lange, Holzminden (DE); Ricarda Kraeling, Holzminden (DE)

(73) Assignee: Symrise AG, Holzminden (DE)

( * ) Notice: Subject to any disclaimer, the term of this patent is extended or adjusted under 35 U.S.C. 154(b) by 538 days.

(21) Appl. No.: 18/044,519

(22) PCT Filed: Sep. 10, 2020

(86) PCT No.: PCT/EP2020/075419

§ 371 (c)(1),
(2) Date: Mar. 8, 2023

(87) PCT Pub. No.: WO2022/053140

PCT Pub. Date: Mar. 17, 2022

(65) Prior Publication Data

US 2023/0329994 A1 Oct. 19, 2023

(51) Int. Cl.
*A61K 8/49* (2006.01)
*A61K 8/68* (2006.01)

(52) U.S. Cl.
CPC .............. *A61K 8/4913* (2013.01); *A61K 8/68* (2013.01); *A61K 2800/596* (2013.01)

(58) Field of Classification Search
CPC .................... A61K 8/4913; A61K 8/68; A61K 2800/596; A61K 8/731
See application file for complete search history.

(56) References Cited

U.S. PATENT DOCUMENTS

2006/0060612 A1 3/2006 Antal

FOREIGN PATENT DOCUMENTS

| | | | | |
|---|---|---|---|---|
| DE | 4308794 | C1 | | 4/1994 |
| DE | 0864563 | | * | 9/1998 |
| EP | 0864563 | A1 | | 9/1998 |
| EP | 0750606 | B1 | | 10/1998 |
| ES | 1816998 | B1 | * | 3/2009 |
| ES | 2321218 | | * | 3/2009 |
| JP | 2015093840 | A | | 5/2015 |
| JP | 2015221755 | A | | 12/2015 |
| WO | 9101295 | A1 | | 2/1991 |
| WO | 9400127 | A1 | | 1/1994 |
| WO | 9821176 | A1 | | 5/1998 |
| WO | 2006053912 | A | | 5/2006 |
| WO | 2015152420 | A1 | | 10/2015 |
| WO | WO201515240 | | * | 10/2015 |
| WO | WO2015152420 | | * | 10/2015 |

OTHER PUBLICATIONS

G. Vielhaber, et al., 2005, “N-Palmitoyl-4-hydroxy-I-proline palmityl ester: A pseudoceramide that provides efficient skin barrier repair and protection” Intl. Journ. of Cosmetic Science, vol. 28, pp. 69-71.
Symrise/Haarmann & Reimer GmbH et al., 2003 “N-Acyl-hydroxyaminosäureester in kosmetischen und dermatologischen Zubereitungen”, Research Disclosure, Kenneth Mason Publications, vol. 468, No. 117.
M. Kucharekova, et al., 2002, “Effect of a lipid-rich emollient containing ceramide 3 in experimentally induced skin barrier dysfunction”, Contact Dermatitis, vol. 46, pp. 331-338.
H. Surburg, et al., 2016, “Common fragrance and flavor materials”, 6th edition Wiley-VCH. 382 pages.
Use of pterocarpans and/or Pao rosa heartwood extract as active anti-irritant and/or anti-oxidant ingredients, ip.com Journal, ip.com Inc., West Henrietta, NY, US, Jan. 4, 2012 (Jan. 4, 2012), XP013148792, ISSN: 1533-0001.

* cited by examiner

*Primary Examiner* — Robert A Wax
*Assistant Examiner* — Kimberly Barber
(74) *Attorney, Agent, or Firm* — McDonnell Boehnen Hulbert & Berghoff LLP

(57) ABSTRACT

The present invention relates to a surfactant containing formulation comprising a particular N-acyl-hydroxyamino acid ester and said formulations for personal care such as cosmetic or pharmaceutical, in particular dermatological, formulations. Additionally, the present invention relates to the use of said formulation for strengthening the barrier function of the skin, hair, scalp and nails. Finally, the present invention pertains to the use of at least one particular N-acyl hydroxyamino acid ester for the preparation of a surfactant containing formulation.

20 Claims, 3 Drawing Sheets

| | Visual appearance |
|---|---|
| After preparation |  |
| 3 days 5°C |  |
| 3 days room temperature and darkness |  |

* $p < 0.05$ when compared to indicated groups (Ceramide 2 - 0.05 %, Placebo, and non-treated)

SURFACTANT CONTAINING FORMULATION OF PSEUDO-CERAMIDES

CROSS-REFERENCE TO RELATED APPLICATIONS

This application is the US national phase under 35 U.S.C. § 371 of International Application No. PCT/EP2020/075419, filed Sep. 10, 2020, the contents of which are hereby incorporated by reference in their entirety.

TECHNICAL FIELD

The present invention relates to a surfactant containing formulation comprising a particular N-acyl-hydroxyamino acid ester and said formulations for personal care such as cosmetic or pharmaceutical, in particular dermatological, formulations. Additionally, the present invention relates to the use of said formulation for strengthening the barrier function of the skin, hair, scalp and nails. Finally, the present invention pertains to the use of at least one particular N-acyl hydroxyamino acid ester for the preparation of a surfactant containing formulation.

BACKGROUND ART

The skin is the largest organ of the body. It protects the body from uncontrolled water loss and environmentally induced mechanical, physical, biological and chemical stress. The human skin consists of three layers, the epidermis, dermis and subcutis, as well as the skin appendages such as hair follicles, sebaceous and sweat glands. The epidermis is the interface between the organism and its environment and protects the body from dehydration and from the penetration of harmful influences such as pathogens and sunlight. This protective function is primarily fulfilled by the so-called epidermal permeability barrier.

This outermost epidermal skin layer consists of the stratum corneum and, depending on the body area, is made of a compact composite. This is composed of corneocytes and intercellular lipids. The intercellular lipids in turn consist of three main fractions: Ceramides (about 30 percent), free fatty acids (about 30 percent) and cholesterol and its derivatives. Ceramides are a subgroup of sphingolipids, which belong to the lipids. They consist of an unsaturated amino alcohol (sphingosine) and a fatty acid bound via an amide group.

In addition, ceramides constituting intercellular lipids are also present in the hair. Hair consists of medulla, coltex and cuticle, and most of the hair is coltex made of keratin protein. When the keratin protein of coltex is lost, the hair becomes weak with symptoms such as hair loosening or hair breakage. In order to prevent the loss of the keratin protein of coltex, it is necessary to protect and improve the hair cuticle of the hair. The stratum corneum of the skin and the cuticle of the hair perform similar functions.

The hair cuticle is a thin layer on the outermost layer of hair and takes the form of a layered layer to protect the keratin protein of the coltex and prevents the hair form being damaged and functions as a barrier for protecting the hair from externa stimuli such as perm, dye and dryer. The ceramides exist in the hair cuticles and perform functions of strengthening and protecting internal tissues of the hair.

The ceramide class of lipids is of particular importance here, as ceramides account for almost 50% of the weight share of the barrier lipids. On the other hand, special ceramides with a long-chain omega-hydroxy fatty acid (C30-C32) facilitate the covalent binding to glutamate residues of surface proteins of corneal cells. This ensures that the permeability barrier has a particularly rigid structure and thus protects the skin from drying out and prevents the penetration of foreign substances.

A number of factors are known which reduce or damage the barrier function of the skin, hair, scalp and nails, including excessive treatment with detergents or solvents, irradiation with UV light or excessively low atmospheric humidity.

A disturbance of this natural barrier leads to dry skin, causing itchy, flaky skin or even to pathological skin symptoms such as dermatoses. Finally, it has been observed that the barrier function of the skin deteriorates with increasing age.

If the barrier function is reduced, topically applied substances such as allergens and irritants can penetrate more easily into the skin, into the hair or into the nails, where they can develop more server effects than in undamaged skin. Attempts have therefore already been made to strengthen the barrier function of the skin or hair in order to prevent allergic and irritant skin reactions or repair skin by providing active substances such as (alpha-)bisabolol, panthenol, stimulators of biosynthesis etc.

Another possible way to prevent or repair such skin, hair, scalp or nail conditions is the topical application of dermatological compositions containing ceramide and pseudoceramide [Kucharekova M. et al. (2002), *Contact Dermatitis* 46 (6), 331-338; Coderch L. et al. (2002) *Contact Dermatitis* 47 (3), 139-146; Park et al. (2001) *Kosmetik & Körperpflege* 116 (6), 65-76; Park et al. (2001) *SOFW-Journal* 127, 10-18]. Such amphiphilic compounds can be incorporated particularly well into the extracellular matrix of the skin lipid barrier.

Ceramides and pseudoceramides, i.e. synthetic ceramides, are amphiphilic waxy lipid molecules consisting of a polar head group and a non-polar tail, made up of two optionally hydroxyl-substituted long (≥C6) alkyl or alkenyl chains. A ceramide is composed of sphingosine and a fatty acid:

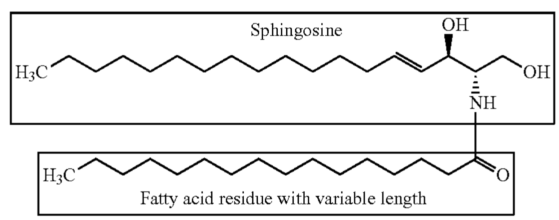 [SMILES: CCCCCCCCCCCCC/C=C/[C@@H](O)[C@H](CO)NC(=O)CCCCCCCCCCCCCCC]

Ceramides and pseudo ceramides (ceramide analogues) have a molecular weight that is below 1000, so that when externally applied in a cosmetic formulation, the active substance can reach the skin lipid barrier. The external application of ceramides or pseudo ceramides leads to the restoration of the skin, hair and nails lipid barrier, whereby the above described disturbance of the function can be reduced or eliminated. These intensive moisturizers can reduce fine lines and wrinkles, prevent dry skin and keep hair soft and healthy. Additionally, pseudoceramide skin care products can even repair the stratum corneum.

The importance of ceramide is widely known. However, natural ceramides are difficult to isolate and they are also laborious and expensive to synthesize.

US 00 606 0612 A describes the synthesis of 1,3-bis (N-(2-hydroxyalkyl) acylamino)-2-hydroxyalkanes as pseudoceramides and their cosmetic use.

WO 98 21176 A1 describes the preparation of N-(2-hydroxyethyl)-3-oxo-2-alkylalkylamides and their cosmetic use for the protection against skin ageing and for strengthening the resistance of skin and hair and for repairing them.

EP 0 864 563 A1 describes the use of N-acyl hydroxy amino acid esters, especially N-acyl hydroxyproline and N-acyl hydroxythreonine esters, to strengthen the natural barrier function to protect against external influences and irritations.

Other examples for pseudoceramides are described in Müller H., 2002, *The Chemistry of Natural and Synthetic Skin Barrier Lipids*, in: Jungermann E., *Kosmetische Wissenschaft und Technologie*, volume 24, as well as in *Kosmetische Lipide und die Hautbarriere*, Marcel Dekker, New York Basel, 2002, 1-35.

WO 9400127 A1 describes the use of a therapeutically effective mixture of cholesterol, ceramides, an essential fatty acid and a non-essential fatty acid with a C12 to C20 alkyl chain for the restoration of the epidermal barrier function of damaged skin.

WO 2006/053912 A1 reveals preparations comprising ceramides and/or pseudoceramides in combination with (alpha-)bisabolol for the prevention of skin damage.

Up to now, ceramides or pseudoceramides are solely used in dermatology, as cosmetics and pharmaceuticals for topical application in the form of solutions, lotions or emulsions but not in surfactant formulations.

Some pseudoceramides, such as Ceramide 2, represented by the formula (with enantiomers):

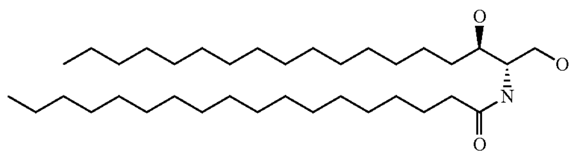 [SMILES: CCCCCCCCCCCCCCCCCC(=O)N[C@@H](CO)[C@H](O)CCCCCCCCCCCCCCC]

or Ceramide 3, represented by the formula (with enantiomers):

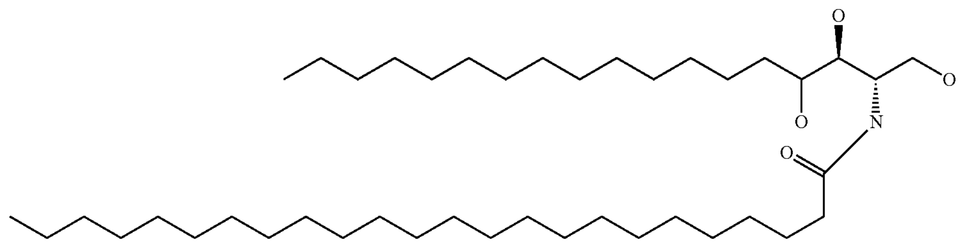 [SMILES: CCCCCCCCCCCCCCCCCCCCCCCC(=O)N[C@@H](CO)[C@H](O)C(O)CCCCCCCCCCCCCC]

for structural reasons have the disadvantage that they are difficult to dissolve, i.e. have poor solubility and instability in a formulation, resulting in precipitation in the formulation, and thus, turbidity. Thus, it is difficult to use the ceramide 2 and ceramide 3 at a high concentration in said formulations.

In particular, the aforementioned pseudoceramides have significantly low solubility in surfactant formulations for skin care such as detergent skin or detergent hair care preparations due to their high lipophilic structure and their high melting point: Ceramide 2: 93 to 96° C.; Ceramide 3: 98 to 110° C.

In order to solve the pseudoceramides in the surfactant formulations, said formulations must be heated above the melting point of said pseudoceramides. Due to the high melting point, the pseudoceramides tend to re-crystallisation upon cooling.

Alternatively, the pseudoceramides in practice are used in combination with a solvent, such as hexyldecanol, optionally with further ingredients such as (alpha-)bisabolol and phytosterol. However, since hexyldecanol is a very lipophilic substance, the addition to a surfactant composition results in a breakdown of the surfactant composition and leads to a turbid unstable solution with decreased viscosity.

It is therefore an object of the present invention to provide a surfactant containing formulation, in particular a ready-for-use formulation, comprising a pseudoceramide compound with improved solubility and stability, so that the pseudoceramide does not precipitate during storage and does not lead to turbididty.

It is another object of the present invention to provide a surfactant containing formulation, comprising a pseudoceramide compound, that is available in the surfactant containing formulation in a high concentration, resulting in an improved bioavailability of the pseudoceramides, for strengthening the barrier function of the skin, hair, scalp and nails.

Surprisingly, it was found that a surfactant containing formulation can be prepared by using a special pseudoceramide compound as described and defined below which can easy be formulated due to a low melting range, has an excellent solubility and stability and does not lead to re-crystallization or turbidity.

SUMMARY OF THE INVENTION

In order to accomplish the above problem, the present invention provides in a first aspect a surfactant containing formulation, comprising or consisting of (a) ≥5% by weight, in particular ≥7% by weight, of at least one surfactant, based on the total weight of the formulation, (b) at least one N-acyl-hydroxyamino acid ester of the general Formula (I)

Formula (I)

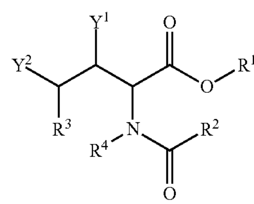

or an enantiomer thereof, wherein

R1 is a linear, branched or cyclic alkyl or alkenyl group having 5 to 50 carbon atoms and optionally substituted by one or more hydroxyl group(s), particularly a linear, branched or cyclic alkyl or alkenyl group having 5 to 24 carbon atoms and optionally substituted by 1 to 6 hydroxyl group(s), R2 is a linear or branched alkyl or alkenyl group having 1 to 49 carbon atoms and optionally substituted by one or more hydroxyl group(s), particularly a linear or branched alkyl or alkenyl group having 2 to 23 carbon atoms and optionally substituted by 1 to 6 hydroxyl group(s), more particular a linear or branched alkyl or alkenyl group having 2 to 23 carbon atoms and optionally substituted by 1 to 3 hydroxyl group(s), Y1 and Y2 are independently of one another, hydrogen or a hydroxyl group, particularly only one of the two groups Y1 and Y2 is a hydroxyl group and the other is a hydrogen atom, R3 and R4 are either independently of one another, hydrogen or a linear or branched alkyl or alkenyl group having 1 to 10 carbon atoms, particularly hydrogen or a linear or branched alkyl or alkenyl group having 1 to 4 carbon atoms, in particular hydrogen, methyl or ethyl, especially hydrogen, or R3 and R4 together are an alkyl group having 1 to 3 carbon atoms or together with the chain between R3 and R4 form a 5- to 7-membered heterocyclic ring, wherein the alkyl group is optionally substituted by 1 to 3 linear or branched alkyl or alkenyl group(s) or is substituted by 1 to 3 hydroxyl group(s); and (c) optionally at least one cosmetically and/or dermatologically active substance and/or additive.

In a second aspect, the present invention provides for the use of the surfactant containing formulation comprising an N-acyl hydroxyamino acid ester of general formula (I) or its enantiomer(s) as defined above for strengthening the barrier function of the skin, hair, scalp and nails or as a cosmetic or pharmaceutical, in particular dermatological, surfactant containing formulation.

Finally, in a still further aspect, the present invention provides a cosmetic or pharmaceutical, preferably a dermatological, surfactant containing formulation.

DETAILED DESCRIPTION OF THE INVENTION

Figure 1:
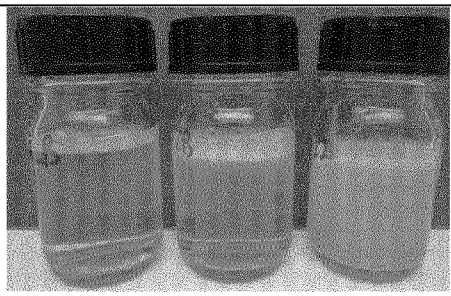
FIG. 1 are photos, showing the solubility of ceramides/pseudoceramides in a surfactant containing formulation after preparation and after storage at 5° C. and at room temperature in darkness.
Figure 1:
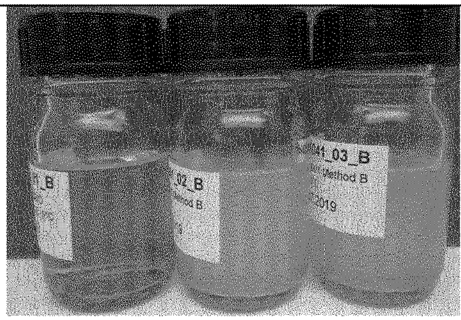
Figure 1:
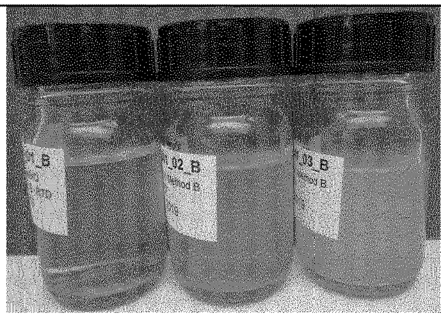

The present invention is specified in the appended claims. The invention itself, and its preferred variants, other objects and advantages, are however also apparent from the following detailed description in conjunction with the accompanying examples and figures.

In a first aspect, the present invention relates to a surfactant containing formulation, comprising or consisting of (a) ≥5% by weight, in particular ≥7% by weight, of at least one surfactant, based on the total weight of the formulation, (b) at least one N-acyl-hydroxyamino acid ester of the general Formula (I)

Formula (I)

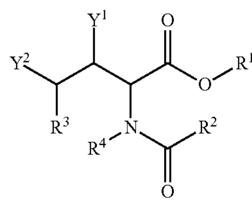

or an enantiomer thereof, wherein

R1 is a linear, branched or cyclic alkyl or alkenyl group having 5 to 50 carbon atoms and optionally substituted by one or more hydroxyl group(s), preferably a linear, branched or cyclic alkyl or alkenyl group having 5 to 24 carbon atoms and optionally substituted by 1 to 6 hydroxyl group(s), R2 is a linear or branched alkyl or alkenyl group having 1 to 49 carbon atoms and optionally substituted by one or more hydroxyl group(s), preferably a linear or branched alkyl or alkenyl group having 2 to 23 carbon atoms and optionally substituted by 1 to 6 hydroxyl group(s), more preferred a linear or branched alkyl or alkenyl group having 2 to 23 carbon atoms and optionally substituted by 1 to 3 hydroxyl group(s), Y1 and Y2 are independently of one another, hydrogen or a hydroxyl group, preferably only one of the two groups Y1 and Y2 is a hydroxyl group and the other is a hydrogen atom, R3 and R4 are either independently of one another, hydrogen or a linear or branched alkyl or alkenyl group having 1 to 10 carbon atoms, preferably hydrogen or a linear or branched alkyl or alkenyl group having 1 to 4 carbon atoms, in particular hydrogen, methyl or ethyl, especially hydrogen, or R3 and R4 together are an alkyl group having 1 to 3 carbon atoms or together with the chain between R3 and R4 form a 5- to 7-membered heterocyclic ring, wherein the alkyl group is optionally substituted by 1 to 3 linear or branched alkyl or alkenyl group(s) or is substituted by 1 to 3 hydroxyl group(s); and (c) optionally at least one cosmetically and/or dermatologically active substance and/or additive.

The term "surfactant" in the context of the present invention means a surfactant or a mixture of surfactants with mainly cleansing and/or foaming properties in a diluted solution.

Surfactants are substances that create self-assembled molecular clusters called micelles in a solution (water or oil phase) and adsorb to the interface between a solution and a different phase (gases/solids). To show these two physical properties, a surfactant must have a chemical structure with tow different functional groups with different affinity within the same molecule. Usually, the molecules of the surfactants have both an alkyl chain with 8 to 22 carbons. This chain is called a hydrophobic group, which does not show affinity to water (they are called hydrophobic groups since surfactants are often used in water systems, but when used in lipid systems they are called lipophilic groups). The surfactant molecules also have a functional group called the hydrophilic group that has affinity to water. This kind of structure with two opposing functions is called an amphiphilic structure.

Surfactants are generally classified according to the nature and charge of the hydrophilic part of the molecule. Surfactants are classified into ionic surfactants and non-ionic surfactants. Ionic surfactants are subclassified into anionc surfactants where the hydrophile group dissociates into anions in aqueous solutions, cationic surfactants that dissociate into cations, and amphoteric or zwitterionic surfactants that dissociate into anions and cations often depending on the pH. Non-ionic surfactants are surfactants that do not dissociate into ions in aqueous solutions, and they are subclassified depending on the type of their hydrophilic group. Common hydrophilic groups of ionic surfactants are carboxylate ($—COO^-$), sulfate ($—OSO_3^-$), sulfonate ($—SO_3^-$), carboxybetaine ($—NR_2CH_2COO^-$), sulfobetaine ($—N(CH_3)_2C_3H_6SO_3^-$) and quaternary ammonium ($—R_4N^+$).

Surfactants are also classified depending on their solubility, such as hydrophilic surfactants that are soluble in water of hydrophobic (lipophilic) substances that are soluble in lipids. Ionic surfactants are generally hydrophilic surfactants, but non-ionic surfactants can be either hydrophilic or lipophilic, depending on the balance of the hydrophilic group and lipophilic group. In other words, the solubility of non-ionic surfactants depends on the balance between the hydrophilic group's capacity of attracting water and the liphilic group's capacity of attracting oil. Hydrophilic-lipophilic balance (HLB) is an indicator that quantifies this relative balance.

Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase.

In the bulk aqueous phase, surfactants form aggregates, such as micelles, where the hydrophobic tails form the core of the aggregate and the hydrophilic heads are in contact with the surrounding liquid. Other types of aggregates can also be formed, such as spherical or cylindrical micelles or lipid layers. The shape of the aggregates depends on the chemical structure of the surfactants, namely the balance in size between the hydrophilic head and hydrophobic tail.

Surfactants form the "heart" in most surfactants formulations and perform many different roles in these systems.

In cosmetics, surfactants play important roles, such as keeping immiscible liquids like oil and water evenly mixed. Their primary function is to remove soils, such as sebum and solid particulates, from the skin, hair, scalp and nails, but they also are important for foaming, building product viscosity, suspending actives and the solubilization of fragrances. Surfactants also play a key role in the performance of systems used to help the system to penetrate skin and hair and deliver actives onto or into the skin, hair, scalp and nails and even keep the system stable for years. Additionally to this, they have to be selected and blended to be as mild to the skin, hair, scalp, nails and eyes as possible. Finally, surfactants change their functions with different concentration, and this makes them essential to cosmetics since they can be utilized to control a product's feeling and functions during the development process.

The surfactant in the surfactant containing formulation according to the present invention is selected from the group consisting of anionic, cationic, non-ionic and amphoteric or zwitterionic surfactants. Preferably, a anionic, non-ionic and/or amphoteric or zwitterionic surfactant is used in the surfactant containing formulation according to present invention.

Anionic surfactants comprise carboxylate, sulphate or sulphonate groups as functional groups. In aqueous solution, they form negatively charged organic ions in the acid or neutral medium. Cationic surfactants are characterised almost exclusively by the presence of a quaternary ammonium group. In aqueous solution, they form positively charged organic ions in the acid or neutral medium. Amphoteric surfactants contain both anionic and cationic groups and accordingly behave like anionic or cationic surfactants in aqueous solution, depending on the pH value. They have a positive charge in a strongly acid medium and a negative charge in an alkaline medium. In the neutral pH range, by contrast, they are zwitterionic. Polyether chains are typical of non-ionic surfactants. Non-ionic surfactants do not form ions in an aqueous medium.

The anionic surfactant that can advantageously be used in the surfactant containing formulation according to the present invention include: acyl amino acids (and their salts), such as: acyl glutamates, for example sodium acyl glutamate, di-TEA-palmitoyl aspartate and sodium caprylic/capric glutamate; acyl peptides, for example palmitoyl-hydrolysed lactoprotein, sodium cocoyl-hydrolysed soy protein and sodium/potassium cocoyl-hydrolysed collagen; sarcosinates, for example myristoyl sarcosinate, TEA-lauroyl sarcosinate, sodium lauroyl sarcosinate and sodium cocoyl sarcosinate; taurates, for example sodium lauroyl taurate and sodium methyl cocoyl taurate; acyl lactylates, for example lauroyl lactylate and caproyl lactylate; alaninates; carboxylic acids and derivatives, such as for example lauric acid, aluminium stearate, magnesium alkanolate and zinc undecylenate; ester carboxylic acids, for example calcium stearoyl lactylate, laureth-6 citrate and sodium PEG-4 lauramide carboxylate; ether carboxylic acids, for example sodium laureth-13 carboxylate and sodium PEG-6 cocamide carboxylate; phosphoric acid esters and salts, such as for example DEA-oleth-10 phosphate and dilaureth-4 phosphate; sulphonic acids and salts, such as acyl isethionates, for example sodium/ammonium cocoyl isethionate; alkyl aryl sulphonates; alkyl sulphonates, for example sodium cocomonoglyceride sulphonate, sodium C12-C14 olefin sulphonate, sodium lauryl sulphoacetate and magnesium PEG-3 cocamide sulphate; sulphosuccinates, for example dioctyl sodium sulphosuccinate, disodium laureth sulphosuccinate, disodium lauryl sulphosuccinate and disodium undecylenamido MEA-sulphosuccinate; and sulphuric acid esters, such as alkyl ether sulphate, for example sodium, ammonium, magnesium, MIPA, TIPA laureth sulphate, sodium myreth sulphate and sodium C12-13 pareth sulphate, and alkyl sulphates, for example sodium, ammonium and TEA lauryl sulphate, or a mixture of two or more of the afore-mentioned anionic surfactants.

Particularly preferred anionic surfactants are selected from the group consisting of ammonium lauryl sulfate, ammonium laureth sulfate, sodium coco-sulfate, sodium laureth sulfate, sodium lauryl sarcosinate, sodium myreth sulfate, sodium pareth sulfate, sodium lauryl sulfate, TIPA-Laureth Sulfate, α olefin sulfonate, sodium cocoyl lactylate, sodium stearyl lactylate, sodium acyl glutamate, sodium/ammonium cocoyl isethionate, sodium lauroyl sarcosinate, sodium cocoyl sarcosinate, sodium methyl cocoyl taurate, -lauroyl lactylate, -caproyl lactylate, disodium cocoyl glutamate, sodium laureth-13 carboxylate, sodium PEG-6 cocamide carboxylate, sodium C12-C14 olefin sulphonate, sodium C14-C16 olefin sulphonate, sodium lauryl sulphoacetate sodium sulphosuccinate, disodium laureth sulphosuccinate, disodium lauryl sulphosuccinate, sodium myreth sulphate, sodium C12-C13 pareth sulphate, sodium, ammonium- and TEA lauryl sulphate, sodium lauroyl methyl isethionate, sodium lauroamphoacetate, cocamide MIPA sodium lauroyl methyl isethionate, sodium lauroamphoacetate, sodium xylene sulfonate, sodium hydrolyzed potato starch dodecenylsuccinate, and a mixture of two or more of the afore-mentioned anionic surfactants.

Cationic surfactants that can advantageously be used in the surfactant containing formulation according to the present invention include: alkyl amines, alkyl imidazoles, ethoxylated amines and quaternary surfactants. Quaternary surfactants contain at least one N atom that is covalently bonded to four alkyl or aryl groups. This leads to a positive charge, irrespective of the pH value. Alkyl betaine, alkyl amidopropyl betaine and alkyl amidopropyl hydroxysulphaine are advantageous. The cationic surfactants used can also preferably be chosen from the group of quaternary ammonium compounds, in particular benzyl trialkyl ammonium chlorides or bromides, such as for example benzyl dimethylstearyl ammonium chloride, as well as alkyl trialkyl ammonium salts, for example cetyl trimethyl ammonium chloride or bromide, alkyl dimethyl hydroxyethyl ammonium chlorides or bromides, dialkyl dimethyl ammonium chlorides or bromides, alkyl amide ethyl trimethyl ammonium ether sulphates, alkyl pyridinium salts, for example lauryl or cetyl pyridinium chloride, imidazoline derivatives and compounds of a cationic nature, such as amine oxides, for example alkyl dimethyl amine oxides or alkyl aminoethyl dimethyl amine oxides. Cetyl trimethyl ammonium salts can particularly advantageously be used.

Particularly preferred cationic surfactants are selected from the group consisting of benzyl dimethylstearyl ammonium chloride, cetrimonium chloride, trimethyl ammonium chloride or bromide, lauryl or cetyl pyridinium chloride, alkyl dimethyl amine oxides or alkyl aminoethyl dimethyl amine oxides, benzalkonium chloride, polyquaternium-6, polyquaternium-7, polyquaternium-10, polyquaternium-22, polyquaternium-37, cocamide MEA, guar hydroxypropyltrimonium chloride, TEA-dodecylbenzenesulfonate, and a mixture of two or more of the afore-mentioned cationic surfactants.

Non-ionic surfactants that can advantageously be used in the surfactant containing formulation according to the present invention include: alcohols; alkanolamides, such as cocamides MEA/DEA/MIPA, amine oxides, such as cocoamidopropylamine oxide; esters formed by esterification of carboxylic acids with ethylene oxide, glycerol, sorbitan or other alcohols; ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and cocoglycoside; sucrose esters and ethers; polyglycerol esters, diglycerol esters, monoglycerol esters; methyl glucose esters and ester of hydroxy acids.

Particularly preferred non-ionic surfactants are selected from the group consisting of cocamide MEA, cocamide DEA, cocamide MIPA, lauryl glucoside, decyl glycoside coco glycoside, PEG-40 hydrogenated castor oil, trideceth-9, polysorbate-20, polysorbate-60, polysorbate-80, laureth-2, laureth-4, PEG-7 glyceryl cocoate, cetearyl glucoside, lauramide DEA, lauramide MEA, glycol distearate, PEG-200-hydrogenated glyceryl palmate, PEG-120 methyl glucose dioleate, sorbitan sesquicaprylate; and mixtures of two or more of the afore-mentioned non-ionic surfactants.

Amphoteric or zwitterionic surfactants that can advantageously be used in the surfactant containing formulation according to the present invention include: acyl/dialkyl ethylene diamine, for example sodium acyl amphoacetate, disodium acyl amphodipropionate, disodium alkyl amphodiacetate, sodium acyl amphohydroxypropyl sulphonate, disodium acyl amphodiacetate and sodium acyl amphopropionate; N-alkyl amino acids, for example aminopropyl alkyl glutamide, alkyl aminopropionic acid, sodium alkyl imidodipropionate, lauroamphocarboxyglycinate, or mixtures of two or more of the afore-mentioned amphoteric surfactants.

Preferred and typical examples for anionic, cationic, non-ionic or amphoteric or zwitterionic surfactants encompass: Almondamidopropylamine Oxide, Almondamidopropyl Betaine, Aminopropyl Laurylglutamine, Ammonium C12-15 Alkyl Sulfate, Ammonium C12-16 Alkyl Sulfate, Ammonium Capryleth Sulfate, Ammonium Cocomonoglyceride Sulfate, Ammonium Coco-Sulfate, Ammonium Cocoyl Isethionate, Ammonium Cocoyl Sarcosinate, Ammonium C12-15 Pareth Sulfate, Ammonium C9-10 Perfluoroalkylsulfonate, Ammonium Dinonyl Sulfosuccinate, Ammonium Dodecylbenzenesulfonate, Ammonium Isostearate, Ammonium Laureth-6 Carboxylate, Ammonium Laureth-8 Carboxylate, Ammonium Laureth Sulfate, Ammonium Laureth-5 Sulfate, Ammonium Laureth-7 Sulfate, Ammonium Laureth-9 Sulfate, Ammonium Laureth-12 Sulfate, Ammonium Lauroyl Sarcosinate, Ammonium Lauryl Sulfate, Ammonium Lauryl Sulfosuccinate, Ammonium Myreth Sulfate, Amium Myristyl Sulfate, Ammonium Nonoxynol-4 Sulfate, Ammonium Nonoxynol-30 Sulfate, Ammonium Oleate, Ammonium Palm Kernel Sulfate, Ammonium Stearate, Ammonium Tallate, AMPD-Isostearoyl Hydrolyzed Collagen, AMPD-Rosin Hydrolyzed Collagen, AMP-Isostearoyl Hydrolyzed Collagen, AMP-Isostearoyl Hydrolyzed Keratin, AMP-Isostearoyl Hydrolyzed Soy Protein, AMP-Isostearoyl Hydrolyzed Wheat Protein, Apricotamidopropyl Betaine, Arachidic Acid, Arginine Hexyldecyl Phosphate, Avocadamidopropyl Betaine, Avocado Oil Glycereth-8 Esters, Babassu Acid, Babassuamidopropylamine Oxide, Babassuamidopropyl Betaine, Beeswax Acid, Behenamidopropyl Betaine, Behenamine Oxide, Beheneth-25, Beheneth-30, Behenic Acid, Behenyl Betaine, Bis-Butyldimethicone Polyglyceryl-3, Butoxynol-5 Carboxylic Acid, Butoxynol-19 Carboxylic Acid, Butyldimonium-hydroxypropyl Butylglucosides Chloride, Butyldimonium-hydroxypropyl Laurylglucosides Chloride, Butyl Glucoside, Butylglucoside Caprate, Butylglucosides Hydroxypropyltrimonium Chloride, Butyloctanoic Acid, C18-36 Acid, C20-40 Acid, C30-50 Acid, C16-22 Acid Amide MEA, Calcium Dodecylbenzenesulfonate, Calcium Lauroyl Taurate, C9-16 Alkane/Cycloalkane, C10-14 Alkyl Benzenesulfonic Acid, C12-14 Alkyl Diaminoethylglycine HCL, C9-15 Alkyl Phosphate, *Candida bombicola*/Glucose/Methyl Rapeseedate Ferment, Canolamidopropyl Betaine, Capric Acid, Caproic Acid, Caproyl Ethyl Glucoside, Capryl/Capramidopropyl Betaine, Capryleth-4 Carboxylic Acid, Capryleth-6 Carboxylic Acid, Capryleth-9 Carboxylic Acid, Caprylic Acid, Capryloyl Collagen Amino Acids, Capryloyl Glycine, Capryloyl Hydrolyzed Collagen, Capryloyl Hydrolyzed Keratin, Capryloyl Keratin Amino Acids, Capryloyl Silk Amino Acids, Caprylyl/Capryl Glucoside, Caprylyl/Capryl Wheat Bran/Straw Glycosides, Caprylyl Glucoside, Caprylyl Glyceryl Ether, Caprylyl Pyrrolidone, Carnitine, Ceteareth-20, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Ceteareth-55, Ceteareth-60, Ceteareth-80, Ceteareth-100, Ceteareth-25 Carboxylic Acid, Ceteareth-2 Phosphate, Ceteareth-4 Phosphate, Ceteareth-5 Phosphate, Ceteareth-10 Phosphate, Ceteth-20, Ceteth-23, Ceteth-24, Ceteth-25, Ceteth-30, Ceteth-40, Ceteth-45, Ceteth-150, Ceteth-8 Phosphate, Ceteth-10 Phosphate, Ceteth-20 Phosphate, Cetoleth-22, Cetoleth-24, Cetoleth-25, Cetoleth-30, Cetyl Betaine, *Chrysanthemum sinense* Flower Extract, C12-14 Hydroxyalkyl Hydroxyethyl Beta-Alanine, C12-14 Hydroxyalkyl Hydroxyethyl Sarcosine, Cocamidoethyl Betaine, Cocamidopropylamine Oxide, Cocamidopropyl Betainamide MEA Chloride, Cocamidopropyl Betaine, Cocamidopropyl Hydroxysultaine, Cocamine Oxide, Cocaminobutyric Acid, Cocaminopropionic Acid, Coceth-7 Carboxylic Acid, Coceth-4 Glucoside, Cocoamphodipropionic Acid, Cocobetainamido Amphopropionate, Coco-Betaine, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Coco-Glucoside, Cocoglucosides Hydroxypropyltrimonium Chloride, Coco-Hydroxysultaine, Coco-Morpholine Oxide, Coconut Acid, Coconut Oil Glycereth-8 Esters, Coco/Oleamidopropyl Betaine, Coco-Sultaine, Coco/Sunfloweramidopropyl Betaine, Cocoylcholine Methosulfate, Cocoyl Glutamic Acid, Cocoyl Hydrolyzed Collagen, Cocoyl Hydrolyzed Keratin, Cocoyl Hydrolyzed Oat Protein, Cocoyl Hydrolyzed Rice Protein, Cocoyl Hydrolyzed Silk, Cocoyl Hydrolyzed Soy Protein, Cocoyl Hydrolyzed Wheat Protein, Cocoyl Sarcosine, Corn Acid, Cottonseed Acid, Cottonseed Oil Glycereth-8 Esters, C10-16 Pareth-1, C10-16 Pareth-2, C11-13 Pareth-6, C11-13 Pareth-9, C11-13 Pareth-10, C11-15 Pareth-30, C11-15 Pareth-40, C12-13 Pareth-1, C12-13 Pareth-23, C12-14 Pareth-5, C12-14 Pareth-9, C13-15 Pareth-21, C14-15 Pareth-8, C20-22 Pareth-30, C20-40 Pareth-40, C20-40 Pareth-95, C22-24 Pareth-33, C30-50 Pareth-40, C9-11 Pareth-6 Carboxylic Acid, C9-11 Pareth-8 Carboxylic Acid, C11-15 Pareth-7 Carboxylic Acid, C12-13 Pareth-5 Carboxylic Acid, C12-13 Pareth-7 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C12-15 Pareth-12 Carboxylic Acid, C14-15 Pareth-8 Carboxylic Acid, C6-10 Pareth-4 Phosphate, C12-13 Pareth-2 Phosphate, C12-13 Pareth-10 Phosphate, C12-15 Pareth-6 Phosphate, C12-15 Pareth-8 Phosphate, C12-15 Pareth-10 Phosphate, C12-16 Pareth-6 Phosphate, C4-18 Perfluoroalkylethyl Thiohydroxypropyltrimonium Chloride, Cupuassuamidopropyl Betaine, DEA-C12-13 Alkyl Sulfate, DEA-C12-15 Alkyl Sulfate, DEA-Ceteareth-2 Phosphate, DEA-Cetyl Sulfate, DEA-Cocoamphodipropionate, DEA-C12-13 Pareth-3 Sulfate, DEA-Cyclocarboxypropyloleate, DEA-Dodecylbenzenesulfonate, DEA-Isostearate, DEA-Laureth Sulfate, DEA-Lauryl Sulfate, DEA-Linoleate, DEA-Methyl Myristate Sulfonate, DEA-Myreth Sulfate, DEA-Myristate, DEA-Myristyl Sulfate, DEA-Oleth-5 Phosphate, DEA-Oleth-20 Phosphate, DEA PG-Oleate, Deceth-7 Carboxylic Acid, Deceth-7 Glucoside, Deceth-9 Phosphate, Decylamine Oxide, Decyl Betaine, Decyl Glucoside, Decyltetradeceth-30, Decyltetradecylamine Oxide, Diammonium Lauramido-MEA Sulfosuccinate, Diammonium Lauryl Sulfosuccinate, Diammonium Oleamido PEG-2 Sulfosuccinate, Dibutoxymethane, Di-Cl 2-15 Pareth-2 Phosphate, Di-Cl 2-15 Pareth-4 Phosphate, Di-Cl 2-15 Pareth-6 Phosphate, Di-C12-15 Pareth-8 Phosphate, Di-Cl 2-15 Pareth-10 Phosphate, Didodecyl Butanetetracarboxylate, Diethylamine Laureth Sulfate, Diethylhexyl Sodium Sulfosuccinate, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Dimethicone PEG-7 Phosphate, Dimethicone PEG-10 Phosphate, Dimethicone PEG/PPG-7/4 Phosphate, Dimethicone PEG/PPG-12/4 Phosphate, Dimethicone/Polyglycerin-3 Crosspolymer, Dimethicone Propyl PG-Betaine, Dimyristyl Phosphate, Dioleoylamidoethyl Hydroxyethylmonium Methosulfate, DIPA-Hydrogenated Cocoate, DIPA-Lanolate, DIPA-Myristate, Dipotassium Capryloyl Glutamate, Dipotassium Lauryl Sulfosuccinate, Dipotassium Undecylenoyl Glutamate, Disodium Babassuamido MEA-Sulfosuccinate, Disodium Caproamphodiacetate, Disodium Caproamphodipropionate, Disodium Capryloamphodiacetate, Disodium Capryloamphodipropionate, Disodium Capryloyl Glutamate, Disodium Cetearyl Sulfosuccinate, Disodium Cetyl Phenyl Ether Disulfonate, Disodium Cetyl Sulfosuccinate, Disodium Cocamido MEA-Sulfosuccinate, Disodium Cocamido MIPA PEG-4 Sulfosuccinate, Disodium Cocamido MIPA-Sulfosuccinate, Disodium Cocamido PEG-3 Sulfosuccinate, Disodium Coceth-3 Sulfosuccinate, Disodium Cocoamphocarboxyethylhydroxypropylsulfonate, Disodium Cocoamphodiacetate, Disodium Cocoamphodipropionate, Disodium Coco-Glucoside Sulfosuccinate, Disodium Coco-Sulfosuccinate, Disodium Cocoyl Butyl Gluceth-10 Sulfosuccinate, Disodium Cocoyl Glutamate, Disodium C12-14 Pareth-1 Sulfosuccinate, Disodium C12-14 Pareth-2 Sulfosuccinate, Disodium C12-15 Pareth Sulfosuccinate, Disodium C12-14 Sec-Pareth-3 Sulfosuccinate, Disodium C12-14 Sec-Pareth-5 Sulfosuccinate, Disodium C12-14 Sec-Pareth-7 Sulfosuccinate, Disodium C12-14 Sec-Pareth-9 Sulfosuccinate, Disodium C12-14 Sec-Pareth-12 Sulfosuccinate, Disodium Deceth-5 Sulfosuccinate, Disodium Deceth-6 Sulfosuccinate, Disodium Decyl Phenyl Ether Disulfonate, Disodium Dihydroxyethyl Sulfosuccinylundecylenate, Disodium Ethylene Dicocamide PEG-15 Disulfate, Disodium Hydrogenated Cottonseed Glyceride Sulfosuccinate, Disodium Hydrogenated Tallow Glutamate, Disodium Hydroxydecyl Sorbitol Citrate, Disodium Isodecyl Sulfosuccinate, Disodium Isostearamido MEA-Sulfosuccinate, Disodium Isostearamido MIPA-Sulfosuccinate, Disodium Isostearoamphodiacetate, Disodium Isostearoamphodipropionate, Disodium Isostearyl Sulfosuccinate, Disodium Laneth-5 Sulfosuccinate, Disodium Lauramido MEA-Sulfosuccinate, Disodium Lauramido MIPA Glycol Sulfosuccinate, Disodium Lauramido PEG-2 Sulfosuccinate, Disodium Lauramido PEG-5 Sulfosuccinate, Disodium Laureth-5 Carboxyamphodiacetate, Disodium Laureth-7 Citrate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauriminobishydroxypropylsulfonate, Disodium Lauriminodiacetate, Disodium Lauriminodipropionate, Disodium Lauriminodipropionate Tocopheryl Phosphates, Disodium Lauroamphodiacetate, Disodium Lauroamphodipropionate, Disodium N-Lauroyl Aspartate, Disodium Lauroyl Glutamate, Disodium Lauryl Phenyl Ether Disulfonate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleoamphodipropionate, Disodium Oleth-3 Sulfosuccinate, Disodium Oleyl Phosphate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-12 Dimethicone Sulfosuccinate, Disodium PEG-8 Palm Glycerides Sulfosuccinate, Disodium PPG-2-Isodeceth-7 Carboxyamphodiacetate, Disodium Ricinoleamido MEA-Sulfosuccinate, Disodium Sitostereth-14 Sulfosuccinate, Disodium Soyamphodiacetate, Disodium Stearamido MEA-Sulfosuccinate, Disodium Steariminodipropionate, Disodium Stearoamphodiacetate, Disodium Stearoyl Glutamate, Disodium Stearyl Sulfosuccinamate, Disodium Stearyl Sulfosuccinate, Disodium 2-Sulfolaurate, Disodium 2-Sulfopalmitate, Disodium Tallamido MEA-Sulfosuccinate, Disodium Tallowamido MEA-Sulfosuccinate, Disodium Tallowamphodiacetate, Disodium Tallowiminodipropionate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Undecylenoyl Glutamate, Disodium Wheat Germamido MEA-Sulfosuccinate, Disodium Wheat Germamido PEG-2 Sulfosuccinate, Disodium Wheatgermamphodiacetate, Di-TEA-Cocamide Diacetate, Di-TEA-Oleamido PEG-2 Sulfosuccinate, Di-TEA-Palmitoyl Aspartate, Ditridecyl Sodium Sulfosuccinate, Dodecylbenzene Sulfonic Acid, Erucamidopropyl Hydroxysultaine, Ethylhexeth-3 Carboxylic Acid, Ethyl PEG-15 Cocamine Sulfate, Glyceryl Capryl Ether, Hexyldecanoic Acid, Hydrogenated Coconut Acid, Hydrogenated Laneth-25, Hydrogenated Menhaden Acid, Hydrogenated Palm Acid, Hydrogenated Palm Kernel Amine Oxide, Hydrogenated Tallow Acid, Hydrogenated Tallowamine Oxide, Hydrogenated Tallow Betaine, Hydrogenated Talloweth-25, Hydrogenated Tallowoyl Glutamic Acid, Hydrolyzed *Candida Bombicola* Extract, Hydroxyceteth-60, Hydroxyethyl Acetomonium PG-Dimethicone, Hydroxyethylbutylamine Laureth Sulfate, Hydroxyethyl Carboxymethyl Cocamidopropylamine, Hydroxyethyl Hydroxypropyl C12-15 Alkoxypropylamine Oxide, Hydroxylauryl/Hydroxymyristyl Betaine, Hydroxystearic Acid, Hydroxysuccinimidyl C10-40 Isoalkyl Acidate, Hydroxysuccinimidyl C21-22 Isoalkyl Acidate, Hydroxysultaines, IPDI/PEG-15 Soyamine Oxide Copolymer, IPDI/PEG-15 Soyethonium Ethosulfate Copolymer, IPDI/PEG-15 Soy Glycinate Copolymer, Isoceteth-30, Isolaureth-4 Phosphate, Isopolyglyceryl-3 Dimethicone, Isopolyglyceryl-3 Dimethiconol, Isopropanolamine Lanolate, Isopropylamine Dodecylbenzenesulfonate, Isostearamidopropylamine Oxide, Isostearamidopropyl Betaine, Isostearamidopropyl Morpholine Oxide, Isosteareth-8, Isosteareth-16, Isosteareth-22, Isosteareth-25, Isosteareth-50, Isostearic Acid, Isostearoyl Hydrolyzed Collagen, Jojoba Oil PEG-150 Esters, Jojoba Wax PEG-80 Esters, Jojoba Wax PEG-120 Esters, Laneth-20, Laneth-25, Laneth-40, Laneth-50, Laneth-60, Laneth-75, Lanolin Acid, Lauramidopropylamine Oxide, Lauramidopropyl Betaine, Lauramidopropyl Hydroxysultaine, Lauramine Oxide, Lauraminopropionic Acid, Laurdimoniumhydroxypropyl Decylglucosides Chloride, Laurdimoniumhydroxypropyl Laurylglucosides Chloride, Laureth-16, Laureth-20, Laureth-21, Laureth-23, Laureth-25, Laureth-30, Laureth-38, Laureth-40, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Laureth-6 Citrate, Laureth-7 Citrate, Laureth-1 Phosphate, Laureth-2 Phosphate, Laureth-3 Phosphate, Laureth-4 Phosphate, Laureth-7 Phosphate, Laureth-8 Phosphate, Laureth-7 Tartrate, Laurie Acid, Laurimino Bispropanediol, Lauriminodipropionic Acid, Lauroamphodipropionic Acid, Lauroyl Beta-Alanine, Lauroyl Collagen Amino Acids, Lauroyl Ethyltrimonium Methosulfate, Lauroyl Hydrolyzed Collagen, Lauroyl Hydrolyzed Elastin, Lauroyl Methyl Glucamide, Lauroyl Sarcosine, Lauroyl Silk Amino Acids, Lauryl Betaine, Lauryl Dimethicone/Polyglycerin-3 Crosspolymer, Lauryldimoniumhydroxypropyl Cocoglucosides Chloride, Lauryl Glucoside, Laurylglucosides Hydroxypropyltrimonium Chloride, Lauryl Glycol Hydroxypropyl Ether, Lauryl Hydroxysultaine, Lauryl Malamide, Lauryl Methylgluc-amide, Lauryl/Myristyl Glycol Hydroxypropyl Ether, Lauryl/Myristyl Wheat Bran/Straw Glycosides, Lauryl Polyglyceryl-3 Polydimethylsiloxyethyl Dimethicone, Lauryl Pyrrolidone, Lauryl Sultaine, Linoleic Acid, Linolenic Acid, Linseed Acid, Lysine Cocoate, Macadamia Seed Oil Glycereth-8 Esters, Magnesium Coceth Sulfate, Magnesium Coco-Sulfate, Magnesium Isododecylbenzenesulfonate, Magnesium Laureth-11 Carboxylate, Magnesium Laureth Sulfate, Magnesium Laureth-5 Sulfate, Magnesium Laureth-8 Sulfate, Magnesium Laureth-16 Sulfate, Magnesium Laureth-3 Sulfosuccinate, Magnesium Lauryl Hydroxypropyl Sulfonate, Magnesium Lauryl Sulfate, Magnesium Methyl Cocoyl Taurate, Magnesium Myreth Sulfate, Magnesium Oleth Sulfate, Magnesium/TEA-Coco-Sulfate, Manicouagan Clay, MEA-Cocoate, MEA-Laureth-6 Carboxylate, MEA-Laureth Sulfate, MEA-Lauryl Sulfate, MEA PPG-6 Laureth-7 Carboxylate, MEA-PPG-8-Steareth-7 Carboxylate, MEA-Undecylenate, Meroxapol 108, Meroxapol 174, Meroxapol 178, Meroxapol 254, Meroxapol 255, Meroxapol 258, Meroxapol 314, Methoxy PEG-450 Amidoglutaroyl Succinimide, Methoxy PEG-450 Amido Hydroxysuccinimidyl Succinamate, Methoxy PEG-450 Maleimide, Methyl Morpholine Oxide, Milkamidopropyl Amine Oxide, Milkamidopropyl Betaine, Minkamidopropylamine Oxide, Minkamidopropyl Betaine, MIPA C12-15 Pareth Sulfate, MIPA-Dodecylbenzenesulfonate, MIPA-Laureth Sulfate, MIPA-Lauryl Sulfate, Mixed Isopropanolamines Lanolate, Mixed Isopropanolamines Lauryl Sulfate, Mixed Isopropanolamines Myristate, Morpholine Oleate, Morpholine Stearate, Myreth-3 Carboxylic Acid, Myreth-5 Carboxylic Acid, Myristalkonium Chloride, Myristamidopropylamine Oxide, Myristamidopropyl Betaine, Myristamidopropyl Dimethylamine Phosphate, Myristamidopropyl Hydroxysultaine, Myristamidopropyl PG-Dimonium Chloride Phosphate, Myristamine Oxide, Myristaminopropionic Acid, Myristic Acid, Myristoyl Ethyltrimonium Methosulfate, Myristoyl Glutamic Acid, Myristoyl Hydrolyzed Collagen, Myristoyl Sarcosine, Myristyl Betaine, Myristyl/Cetyl Amine Oxide, Myristyldimoniumhydroxypropyl Cocoglucosides Chloride, Myristyl Glucoside, Myristyl Phosphate, Nonoxynol-20, Nonoxynol-23, Nonoxynol-25, Nonoxynol-30, Nonoxynol-35, Nonoxynol-40, Nonoxynol-44, Nonoxynol-50, Nonoxynol-100, Nonoxynol-120, Nonoxynol-5 Carboxylic Acid, Nonoxynol-8 Carboxylic Acid, Nonoxynol-10 Carboxylic Acid, Nonoxynol-3 Phosphate, Nonoxynol-4 Phosphate, Nonoxynol-6 Phosphate, Nonoxynol-9 Phosphate, Nonoxynol-10 Phosphate, Nonyl Nonoxynol-30, Nonyl Nonoxynol-49, Nonyl Nonoxynol-100, Nonyl Nonoxynol-150, Nonyl Nonoxynol-7 Phosphate, Nonyl Nonoxynol-8 Phosphate, Nonyl Nonoxynol-9 Phosphate, Nonyl Nonoxynol-10 Phosphate, Nonyl Nonoxynol-11 Phosphate, Nonyl Nonoxynol-15 Phosphate, Nonyl Nonoxynol-24 Phosphate, Oatamidopropyl Betaine, Octoxynol-16, Octoxynol-25, Octoxynol-30, Octoxynol-33, Octoxynol-40, Octoxynol-70, Octoxynol-20 Carboxylic Acid, Octyldodeceth-20, Octyldodeceth-25, Octyldodeceth-30, Oleamidopropylamine Oxide, Oleamidopropyl Betaine, Oleamidopropyl Hydroxysultaine, Oleamine Oxide, Oleic Acid, Oleoyl Hydrolyzed Collagen, Oleoyl Sarcosine, Oleth-20, Oleth-23, Oleth-24, Oleth-25, Oleth-30, Oleth-35, Oleth-40, Oleth-44, Oleth-50, Oleth-3 Carboxylic Acid, Oleth-6 Carboxylic Acid, Oleth-10 Carboxylic Acid, Oleyl Betaine, Olivamidopropylamine Oxide, Olivamidopropyl Betaine, Olive Acid, Olivoyl Hydrolyzed Wheat Protein, Ophiopogon Extract Stearate, Ozonized Oleth-10, Ozonized PEG-10 Oleate, Ozonized PEG-14 Oleate, Ozonized Polysorbate 80, Palm Acid, Palmamidopropyl Betaine, Palmeth-2 Phosphate, Palm itamidopropylamine Oxide, Palm itamidopropyl Betaine, Palmitamine Oxide, Palmitic Acid, Palmitoyl Collagen Amino Acids, Palmitoyl Glycine, Palmitoyl Hydrolyzed Collagen, Palmitoyl Hydrolyzed Milk Protein, Palmitoyl Hydrolyzed Wheat Protein, Palmitoyl Keratin Amino Acids, Palmitoyl Oligopeptide, Palmitoyl Silk Amino Acids, Palm Kernel Acid, Palm Kernelamidopropyl Betaine, Peach Kernel Oil Glycereth-8 Esters, Peanut Acid, PEG-10 Castor Oil, PEG-40 Castor Oil, PEG-44 Castor Oil, PEG-50 Castor Oil, PEG-54 Castor Oil, PEG-55 Castor Oil, PEG-60 Castor Oil, PEG-80 Castor Oil, PEG-100 Castor Oil, PEG-200 Castor Oil, PEG-11 Cocamide, PEG-6 Cocamide Phosphate, PEG-4 Cocamine, PEG-8 Cocamine, PEG-12 Cocamine, PEG-150 Dibehenate, PEG-90 Diisostearate, PEG-75 Dilaurate, PEG-150 Dilaurate, PEG-75 Dioleate, PEG-150 Dioleate, PEG-75 Distearate, PEG-120 Distearate, PEG-150 Distearate, PEG-175 Distearate, PEG-190 Distearate, PEG-250 Distearate, PEG-30 Glyceryl Cocoate, PEG-40 Glyceryl Cocoate, PEG-78 Glyceryl Cocoate, PEG-80 Glyceryl Cocoate, PEG-30 Glyceryl Isostearate, PEG-40 Glyceryl Isostearate, PEG-50 Glyceryl Isostearate, PEG-60 Glyceryl Isostearate, PEG-90 Glyceryl Isostearate, PEG-23 Glyceryl Laurate, PEG-30 Glyceryl Laurate, PEG-25 Glyceryl Oleate, PEG-30 Glyceryl Oleate, PEG-30 Glyceryl Soyate, PEG-25 Glyceryl Stearate, PEG-30 Glyceryl Stearate, PEG-40 Glyceryl Stearate, PEG-120 Glyceryl Stearate, PEG-200 Glyceryl Stearate, PEG-28 Glyceryl Tallowate, PEG-80 Glyceryl Tallowate, PEG-82 Glyceryl Tallowate, PEG-130 Glyceryl Tallowate, PEG-200 Glyceryl Tallowate, PEG-45 Hydrogenated Castor Oil, PEG-50 Hydrogenated Castor Oil, PEG-54 Hydrogenated Castor Oil, PEG-55 Hydrogenated Castor Oil, PEG-60 Hydrogenated Castor Oil, PEG-80 Hydrogenated Castor Oil, PEG-100 Hydrogenated Castor Oil, PEG-200 Hydrogenated Castor Oil, PEG-30 Hydrogenated Lanolin, PEG-70 Hydrogenated Lanolin, PEG-50 Hydrogenated Palmamide, PEG-2 Isostearate, PEG-3 Isostearate, PEG-4 Isostearate, PEG-6 Isostearate, PEG-8 Isostearate, PEG-10 Isostearate, PEG-12 Isostearate, PEG-20 Isostearate, PEG-30 Isostearate, PEG-40 Isostearate, PEG-26 Jojoba Acid, PEG-40 Jojoba Acid, PEG-15 Jojoba Alcohol, PEG-26 Jojoba Alcohol, PEG-40 Jojoba Alcohol, PEG-35 Lanolin, PEG-40 Lanolin, PEG-50 Lanolin, PEG-55 Lanolin, PEG-60 Lanolin, PEG-70 Lanolin, PEG-75 Lanolin, PEG-85 Lanolin, PEG-100 Lanolin, PEG-150 Lanolin, PEG-75 Lanolin Oil, PEG-2 Lauramide, PEG-3 Lauramine Oxide, PEG-20 Laurate, PEG-32 Laurate, PEG-75 Laurate, PEG-150 Laurate, PEG-70 Mango Glycerides, PEG-20 Mannitan Laurate, PEG-8 Methyl Ether Dimethicone, PEG-120 Methyl Glucose Dioleate, PEG-80 Methyl Glucose Laurate, PEG-120 Methyl Glucose Trioleate, PEG-4 Montanate, PEG-30 Oleamine, PEG-20 Oleate, PEG-23 Oleate, PEG-32 Oleate, PEG-36 Oleate, PEG-75 Oleate, PEG-150 Oleate, PEG-20 Palmitate, PEG-150 Polyglyceryl-2 Tristearate, PEG/PPG-28/21 Acetate Dimethicone, PEG/PPG-24/18 Butyl Ether Dimethicone, PEG/PPG-3/17 Copolymer, PEG/PPG-5/35 Copolymer, PEG/PPG-8/55 Copolymer, PEG/PPG-10/30 Copolymer, PEG/PPG-10/65 Copolymer, PEG/PPG-12/35 Copolymer, PEG/PPG-16/17 Copolymer, PEG/PPG-20/9 Copolymer, PEG/PPG-20/20 Copolymer, PEG/PPG-20/60 Copolymer, PEG/PPG-20/65 Copolymer, PEG/PPG-22/25 Copolymer, PEG/PPG-28/30 Copolymer, PEG/PPG-30-35 Copolymer, PEG/PPG-30/55 Copolymer, PEG/PPG-35/40 Copolymer, PEG/PPG-50/40 Copolymer, PEG/PPG-150/35 Copolymer, PEG/PPG-160/30 Copolymer, PEG/PPG-190/60 Copolymer, PEG/PPG-200/40 Copolymer, PEG/PPG-300/55 Copolymer, PEG/PPG-20/22 Methyl Ether Dimethicone, PEG-26-PPG-30 Phosphate, PEG/PPG-4/2 Propylheptyl Ether, PEG/PPG-6/2 Propylheptyl Ether, PEG-7/PPG-2 Propylheptyl Ether, PEG/PPG-8/2 Propylheptyl Ether, PEG/PPG-10/2 Propylheptyl Ether, PEG/PPG-14/2 Propylheptyl Ether, PEG/PPG-40/2 Propylheptyl Ether, PEG/PPG-10/2 Ricinoleate, PEG/PPG-32/3 Ricinoleate, PEG-55 Propylene Glycol Oleate, PEG-25 Propylene Glycol Stearate, PEG-75 Propylene Glycol Stearate, PEG-120 Propylene Glycol Stearate, PEG-5 Rapeseed Sterol, PEG-10 Rapeseed Sterol, PEG-40 Ricinoleamide, PEG-75 Shea Butter Glycerides, PEG-75 Shorea Butter Glycerides, PEG-20 Sorbitan Cocoate, PEG-20 Sorbitan Isostearate, PEG-40 Sorbitan Lanolate, PEG-75 Sorbitan Lanolate, PEG-10 Sorbitan Laurate, PEG-40 Sorbitan Laurate, PEG-44 Sorbitan Laurate, PEG-75 Sorbitan Laurate, PEG-80 Sorbitan Laurate, PEG-20 Sorbitan Oleate, PEG-80 Sorbitan Palmitate, PEG-40 Sorbitan Stearate, PEG-60 Sorbitan Stearate, PEG-160 Sorbitan Triisostearate, PEG-40 Soy Sterol, PEG-2 Stearamide Carboxylic Acid, PEG-9 Stearamide Carboxylic Acid, PEG-20 Stearate, PEG-23 Stearate, PEG-25 Stearate, PEG-30 Stearate, PEG-32 Stearate, PEG-35 Stearate, PEG-36 Stearate, PEG-40 Stearate, PEG-45 Stearate, PEG-50 Stearate, PEG-55 Stearate, PEG-75 Stearate, PEG-90 Stearate, PEG-100 Stearate, PEG-120 Stearate, PEG-150 Stearate, PEG-45 Stearate Phosphate, PEG-20 Tallate, PEG-50 Tallow Amide, PEG-2 Tallowamide DEA, PEG-20 Tallowate, PEG-66 Trihydroxystearin, PEG-200 Trihydroxystearin, PEG-60 Tsubakiate Glycerides, Pelargonic Acid, Pentadoxynol-200, Pheneth-6 Phosphate, Poloxamer 105, Poloxamer 108, Poloxamer 182, Poloxamer 183, Poloxamer 184, Poloxamer 188, Poloxamer 217, Poloxamer 234, Poloxamer 235, Poloxamer 237, Poloxamer 238, Poloxamer 288, Poloxamer 334, Poloxamer 335, Poloxamer 338, Poloxamine 908, Poloxamine 1508, Polydimethylsiloxy PEG/PPG-24/19 Butyl Ether Silsesquioxane, Polydimethylsiloxy PPG-13 Butyl Ether Silsesquioxane, Polyglyceryl-6 Caprate, Polyglyceryl-10 Dilaurate, Polyglyceryl-20 Heptacaprylate, Polyglyceryl-20 Hexacaprylate, Polyglyceryl-2 Lauryl Ether, Polyglyceryl-10 Lauryl Ether, Polyglyceryl-20 Octaisononanoate, Polyglyceryl-6 Pentacaprylate, Polyglyceryl-10 Pentacaprylate, Polyglyceryl-3 Polydimethylsiloxyethyl Dimethicone, Polyglyceryl-6 Tetracaprylate, Polyglyceryl-10 Tetralaurate, Polyglyceryl-6 Tricaprylate, Polyglyceryl-10 Trilaurate, Polyquaternium-77, Polyquaternium-78, Polyquaternium-79, Polyquaternium-80, Polyquaternium-81, Polyquaternium-82, Pomaderris Kumerahou Flower/Leaf Extract, Poria *Cocos* Extract, Potassium Abietoyl Hydrolyzed Collagen, Potassium Babassuate, Potassium Behenate, Potassium C9-15 Alkyl Phosphate, Potassium C11-15 Alkyl Phosphate, Potassium C12-13 Alkyl Phosphate, Potassium C12-14 Alkyl Phosphate, Potassium Caprate, Potassium Capryloyl Glutamate, Potassium Capryloyl Hydrolyzed Rice Protein, Potassium Castorate, Potassium Cocoate, Potassium Cocoyl Glutamate, Potassium Cocoyl Glycinate, Potassium Cocoyl Hydrolyzed Casein, Potassium Cocoyl Hydrolyzed Collagen, Potassium Cocoyl Hydrolyzed Corn Protein, Potassium Cocoyl Hydrolyzed Keratin, Potassium Cocoyl Hydrolyzed Oat Protein, Potassium Cocoyl Hydrolyzed Potato Protein, Potassium Cocoyl Hydrolyzed Rice Bran Protein, Potassium Cocoyl Hydrolyzed Rice Protein, Potassium Cocoyl Hydrolyzed Silk, Potassium Cocoyl Hydrolyzed Soy Protein, Potassium Cocoyl Hydrolyzed Wheat Protein, Potassium Cocoyl Hydrolyzed Yeast Protein, Potassium Cocoyl PCA, Potassium Cocoyl Sarcosinate, Potassium Cocoyl Taurate, Potassium Cornate, Potassium Cyclocarboxypropyloleate, Potassium Dihydroxyethyl Cocamine Oxide Phosphate, Potassium Dimethicone PEG-7 Phosphate, Potassium Dodecylbenzenesulfonate, Potassium Hempseedate, Potassium Hydrogenated Cocoate, Potassium Hydrogenated Palmate, Potassium Hydrogenated Tallowate, Potassium Hydroxystearate, Potassium Isostearate, Potassium Lanolate, Potassium Laurate, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Laureth Phosphate, Potassium Lauroyl Collagen Amino Acids, Potassium Lauroyl Glutamate, Potassium Lauroyl Hydrolyzed Collagen, Potassium Lauroyl Hydrolyzed Pea Protein, Potassium Lauroyl Hydrolyzed Soy Protein, Potassium Lauroyl PCA, Potassium Lauroyl Pea Amino Acids, Potassium Lauroyl Sarcosinate, Potassium Lauroyl Silk Amino Acids, Potassium Lauroyl Wheat Amino Acids, Potassium Lauryl Phosphate, Potassium Lauryl Sulfate, Potassium Linoleate, Potassium Metaphosphate, Potassium Methyl Cocoyl Taurate, Potassium Myristate, Potassium Myristoyl Glutamate, Potassium Myristoyl Hydrolyzed Collagen, Potassium Octoxynol-12 Phosphate, Potassium Oleate, Potassium Oleoyl Hydrolyzed Collagen, Potassium Olivate, Potassium Olivoyl Hydrolyzed Oat Protein, Potassium Olivoyl Hydrolyzed Wheat Protein, Potassium Olivoyl/Lauroyl Wheat Amino Acids, Potassium Olivoyl PCA, Potassium Palmate, Potassium Palmitate, Potassium Palmitoyl Hydrolyzed Corn Protein, Potassium Palmitoyl Hydrolyzed Oat Protein, Potassium Palmitoyl Hydrolyzed Rice Protein, Potassium Palmitoyl Hydrolyzed Sweet Almond Protein, Potassium Palmitoyl Hydrolyzed Wheat Protein, Potassium Palm Kernelate, Potassium Peanutate, Potassium Rapeseedate, Potassium Ricinoleate, Potassium Safflowerate, Potassium Soyate, Potassium Stearate, Potassium Stearoyl Hydrolyzed Collagen, Potassium Tallate, Potassium Tallowate, Potassium Taurate, Potassium Taurine Laurate, Potassium Trideceth-3 Carboxylate, Potassium Trideceth-4 Carboxylate, Potassium Trideceth-7 Carboxylate, Potassium Trideceth-15 Carboxylate, Potassium Trideceth-19 Carboxylate, Potassium Trideceth-6 Phosphate, Potassium Trideceth-7 Phosphate, Potassium Tsubakiate, Potassium Undecylenate, Potassium Undecylenoyl Hydrolyzed Collagen, Potassium Undecylenoyl Hydrolyzed Rice Protein, PPG-30-Buteth-30, PPG-36-Buteth-36, PPG-38-Buteth-37, PPG-30-Capryleth-4 Phosphate, PPG-10 Cetyl Ether Phosphate, PPG-2 C9-11 Pareth-8, PPG-1-Deceth-5, PPG-3-Deceth-2 Carboxylic Acid, PPG-30 Ethylhexeth-4 Phosphate, PPG-20-Glycereth-30, PPG-2 Hydroxyethyl Coco/Isostearamide, PPG-2-Isodeceth-8, PPG-2-Isodeceth-10, PPG-2-Isodeceth-18, PPG-2-Isodeceth-25, PPG-4-Isodeceth-10, Propyltrimonium Hydrolyzed Collagen, Quaternium-24, Quaternium-52, Quaternium-87, Rapeseed Acid, Rice Bran Acid, Rice Oil Glycereth-8 Esters, Ricinoleamidopropyl Betaine, Ricinoleic Acid, Ricinoleth-40, Safflower Acid, *Sapindus oahuensis* Fruit Extract, *Saponaria officinalis* Root Powder, Saponins, Sekken-K, Sekken-Na/K, Sekken Soji, Sekken Soji-K, Sesame Oil Glycereth-8 Esters, Sesamidopropylamine Oxide, Sesamidopropyl Betaine, Shea Butteramidopropyl Betaine, Shea Butter Glycereth-8 Esters, Sodium Arachidate, Sodium Arganampohoacetate, Sodium Astrocaryum Murumuruate, Sodium Avocadoate, Sodium Babassuamphoacetate, Sodium Babassuate, Sodium Babassu Sulfate, Sodium Behenate, Sodium Bisglycol Ricinosulfosuccinate, Sodium Bis-Hydroxyethylglycinate Coco-Glucosides Crosspolymer, Sodium Bis-Hydroxyethylglycinate Lauryl-Glucosides Crosspolymer, Sodium Borageamidopropyl PG-Dimonium Chloride Phosphate, Sodium Butoxynol-12 Sulfate, Sodium Butylglucosides Hydroxypropyl Phosphate, Sodium C13-17 Alkane Sulfonate, Sodium C14-18 Alkane Sulfonate, Sodium C12-15 Alkoxypropyl Iminodipropionate, Sodium C10-16 Alkyl Sulfate, Sodium C11-15 Alkyl Sulfate, Sodium C12-13 Alkyl Sulfate, Sodium C12-15 Alkyl Sulfate, Sodium C12-18 Alkyl Sulfate, Sodium C16-20 Alkyl Sulfate, Sodium C9-22 Alkyl Sec Sulfonate, Sodium C14-17 Alkyl Sec Sulfonate, Sodium Caprate, Sodium Caproamphoacetate, Sodium Caproamphohydroxypropylsulfonate, Sodium Caproamphopropionate, Sodium Caproyl Methyltaurate, Sodium Caprylate, Sodium Capryleth-2 Carboxylate, Sodium Capryleth-9 Carboxylate, Sodium Capryloamphoacetate, Sodium Capryloamphohydroxypropylsulfonate, Sodium Capryloamphopropionate, Sodium Capryloyl Glutamate, Sodium Capryloyl Hydrolyzed Wheat Protein, Sodium Caprylyl PG-Sulfonate, Sodium Caprylyl Sulfonate, Sodium Castorate, Sodium Ceteareth-13 Carboxylate, Sodium Cetearyl Sulfate, Sodium Ceteth-13 Carboxylate, Sodium Cetyl Sulfate, Sodium Cocamidopropyl PG-Dimonium Chloride Phosphate, Sodium Cocaminopropionate, Sodium Coceth Sulfate, Sodium Coceth-30 Sulfate, Sodium Cocoabutteramphoacetate, Sodium Cocoa Butterate, Sodium Cocoamphoacetate, Sodium Cocoamphohydroxypropylsulfonate, Sodium Cocoamphopropionate, Sodium Cocoate, Sodium Coco/Babassu/Andiroba Sulfate, Sodium Coco/Babassu Sulfate, Sodium Cocoglucosides Hydroxypropyl Phosphate, Sodium Cocoglucosides Hydroxypropylsulfonate, Sodium Coco-Glucoside Tartrate, Sodium Cocoglyceryl Ether Sulfonate, Sodium Coco/Hydrogenated Tallow Sulfate, Sodium Cocoiminodiacetate, Sodium Cocomonoglyceride Sulfate, Sodium Cocomonoglyceride Sulfonate, Sodium Coco PG-Dimonium Chloride Phosphate, Sodium Coco-Sulfate, Sodium Coco Sulfoacetate, Sodium Cocoyl Alaninate, Sodium Cocoyl Amino Acids, Sodium Cocoyl Collagen Amino Acids, Sodium Cocoyl Glutamate, Sodium Cocoyl Glutaminate, Sodium Cocoyl Glycinate, Sodium Cocoyl/Hydrogenated Tallow Glutamate, Sodium Cocoyl Hydrolyzed Collagen, Sodium Cocoyl Hydrolyzed Keratin, Sodium Cocoyl Hydrolyzed Rice Protein, Sodium Cocoyl Hydrolyzed Silk, Sodium Cocoyl Hydrolyzed Soy Protein, Sodium Cocoyl Hydrolyzed Sweet Almond Protein, Sodium Cocoyl Hydrolyzed Wheat Protein, Sodium Cocoyl Hydrolyzed Wheat Protein Glutamate, Sodium Cocoyl Isethionate, Sodium Cocoyl Methylaminopropionate, Sodium Cocoyl Oat Amino Acids, Sodium Cocoyl/Palmoyl/Sunfloweroyl Glutamate, Sodium Cocoyl Proline, Sodium Cocoyl Sarcosinate, Sodium Cocoyl Taurate, Sodium Cocoyl Threoninate, Sodium Cocoyl Wheat Amino Acids, Sodium C12-C14 Olefin Sulfonate, Sodium C14-C16 Olefin Sulfonate, Sodium C14-C18 Olefin Sulfonate, Sodium C16-C18 Olefin Sulfonate, Sodium Cornamphopropionate, Sodium Cottonseedamphoacetate, Sodium C13-C15 Pareth-8 Butyl Phosphate, Sodium C9-C11 Pareth-6 Carboxylate, Sodium C11-C15 Pareth-7 Carboxylate, Sodium C12-C13 Pareth-5 Carboxylate, Sodium C12-C13 Pareth-8 Carboxylate, Sodium C12-C13 Pareth-12 Carboxylate, Sodium C12-C15 Pareth-6 Carboxylate, Sodium C12-C15 Pareth-7 Carboxylate, Sodium C12-C15 Pareth-8 Carboxylate, Sodium C14-C15 Pareth-8 Carboxylate, Sodium C12-C14 Sec-Pareth-8 Carboxylate, Sodium C14-C15 Pareth-PG Sulfonate, Sodium C12-C13 Pareth-2 Phosphate, Sodium C13-C15 Pareth-8 Phosphate, Sodium C9-C15 Pareth-3 Sulfate, Sodium C10-C15 Pareth Sulfate, Sodium C10-C16 Pareth-2 Sulfate, Sodium C12-C13 Pareth Sulfate, Sodium C12-C15 Pareth Sulfate, Sodium C12-C15 Pareth-3 Sulfate, Sodium C13-C15 Pareth-3 Sulfate, Sodium C12-C14 Sec-Pareth-3 Sulfate, Sodium C12-C15 Pareth-3 Sulfonate, Sodium C12-C15 Pareth-7 Sulfonate, Sodium C12-C15 Pareth-15 Sulfonate, Sodium Deceth-2 Carboxylate, Sodium Deceth Sulfate, Sodium Decylbenzenesulfonate, Sodium Decylglucosides Hydroxypropyl Phosphate, Sodium Decylglucosides Hydroxypropylsulfonate, Sodium Dilaureth-7 Citrate, Sodium Dilaureth-10 Phosphate, Sodium Dilinoleamidopropyl PG-Dimonium Chloride Phosphate, Sodium Dilinoleate, Sodium Dioleth-8 Phosphate, Sodium Dodecylbenzenesulfonate, Sodium Ethyl 2-Sulfolaurate, Sodium Glyceryl Oleate Phosphate, Sodium Grapeseedamidopropyl PG-Dimonium Chloride Phosphate, Sodium Grapeseedamphoacetate, Sodium Grapeseedate, Sodium Hempseedamphoacetate, Sodium Hexeth-4 Carboxylate, Sodium Hydrogenated Cocoate, Sodium Hydrogenated Cocoyl Methyl Isethionate, Sodium Hydrogenated Palmate, Sodium Hydrogenated Tallowate, Sodium Hydrogenated Tallowoyl Glutamate, Sodium Hydroxylauryldimonium Ethyl Phosphate, Sodium Hydroxypropyl Palm Kernelate Sulfonate, Sodium Hydroxypropylphosphate Decylglucoside Crosspolymer, Sodium Hydroxypropylphosphate Laurylglucoside Crosspolymer, Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer, Sodium Hydroxystearate, Sodium Isostearate, Sodium Isosteareth-6 Carboxylate, Sodium Isosteareth-11 Carboxylate, Sodium Isostearoamphoacetate, Sodium Isostearoamphopropionate, Sodium N-Isostearoyl Methyltaurate, Sodium Laneth Sulfate, Sodium Lanolate, Sodium Lardate, Sodium Lauramido Diacetate, Sodium Lauraminopropionate, Sodium Laurate, Sodium Laureth-3 Carboxylate, Sodium Laureth-4 Carboxylate, Sodium Laureth-5 Carboxylate, Sodium Laureth-6 Carboxylate, Sodium Laureth-8 Carboxylate, Sodium Laureth-11 Carboxylate, Sodium Laureth-12 Carboxylate, Sodium Laureth-13 Carboxylate, Sodium Laureth-14 Carboxylate, Sodium Laureth-16 Carboxylate, Sodium Laureth-17 Carboxylate, Sodium Laureth Sulfate, Sodium Laureth-5 Sulfate, Sodium Laureth-7 Sulfate, Sodium Laureth-8 Sulfate, Sodium Laureth-12 Sulfate, Sodium Laureth-40 Sulfate, Sodium Laureth-7 Tartrate, Sodium Lauriminodipropionate, Sodium Lauroamphoacetate, Sodium Lauroamphohydroxypropylsulfonate, Sodium Lauroampho PG-Acetate Phosphate, Sodium Lauroamphopropionate, Sodium Lauroyl Aspartate, Sodium Lauroyl Collagen Amino Acids, Sodium Lauroyl Glycine Propionate, Sodium Lauroyl Hydrolyzed Collagen, Sodium Lauroyl Hydrolyzed Silk, Sodium Lauroyl Hydroxypropyl Sulfonate, Sodium Lauroyl Isethionate, Sodium Lauroyl Methylaminopropionate, Sodium Lauroyl Methyl Isethionate, Sodium Lauroyl Millet Amino Acids, Sodium Lauroyl/Myristoyl Aspartate, Sodium Lauroyl Oat Amino Acids, Sodium Lauroyl Sarcosinate, Sodium Lauroyl Silk Amino Acids, Sodium Lauroyl Taurate, Sodium Lauroyl Wheat Amino Acids, Sodium Lauryl Diethylenediaminoglycinate, Sodium Lauryl Glucose Carboxylate, Sodium Laurylglucosides Hydroxypropyl Phosphate, Sodium Laurylglucosides Hydroxypropylsulfonate, Sodium Lauryl Glycol Carboxylate, Sodium Lauryl Hydroxyacetamide Sulfate, Sodium Lauryl Phosphate, Sodium Lauryl Sulfate, Sodium Lauryl Sulfoacetate, Sodium Linoleate, Sodium Macadamiaseedate, Sodium Mangoamphoacetate, Sodium Mangoseedate, Sodium/MEA Laureth-2 Sulfosuccinate, Sodium Methoxy PPG-2 Acetate, Sodium Methyl Cocoyl Taurate, Sodium Methyl Lauroyl Taurate, Sodium Methyl Myristoyl Taurate, Sodium Methyl Oleoyl Taurate, Sodium Methyl Palmitoyl Taurate, Sodium Methyl Stearoyl Taurate, Sodium Methyl 2-Sulfolaurate, Sodium Methyl 2-Sulfopalmitate, Sodium Methyltaurate Isopalmitamide, Sodium Methyltaurine Cocoyl Methyltaurate, Sodium Myreth Sulfate, Sodium Myristate, Sodium Myristoamphoacetate, Sodium Myristoyl Glutamate, Sodium Myristoyl Hydrolyzed Collagen, Sodium Myristoyl Isethionate, Sodium Myristoyl Sarcosinate, Sodium Myristyl Sulfate, Sodium Nonoxynol-6 Phosphate, Sodium Nonoxynol-9 Phosphate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8 Sulfate, Sodium Nonoxynol-10 Sulfate, Sodium Nonoxynol-25 Sulfate, Sodium Octoxynol-2 Ethane Sulfonate, Sodium Octoxynol-2 Sulfate, Sodium Octoxynol-6 Sulfate, Sodium Octoxynol-9 Sulfate, Sodium Oleate, Sodium Oleoamphoacetate, Sodium Oleoamphohydroxypropylsulfonate, Sodium Oleoamphopropionate, Sodium Oleoyl Hydrolyzed Collagen, Sodium Oleoyl Isethionate, Sodium Oleth Sulfate, Sodium Oleyl Methyl Isethionate, Sodium Oleyl Sulfate, Sodium Olivamphoacetate, Sodium Olivate, Sodium Olivoyl Glutamate, Sodium Palmamphoacetate, Sodium Palmate, Sodium Palm Glyceride Sulfonate, Sodium Palmitate, Sodium Palmitoyl Hydrolyzed Collagen, Sodium Palmitoyl Hydrolyzed Wheat Protein, Sodium Palmitoyl Sarcosinate, Sodium Palm Kernelate, Sodium Palm Kerneloyl Isethionate, Sodium Palmoyl Glutamate, Sodium *Passiflora edulis* Seedate, Sodium Peanutamphoacetate, Sodium Peanutate, Sodium PEG-6 Cocamide Carboxylate, Sodium PEG-8 Cocamide Carboxylate, Sodium PEG-4 Cocamide Sulfate, Sodium PEG-3 Lauramide Carboxylate, Sodium PEG-4 Lauramide Carboxylate, Sodium PEG-8 Palm Glycerides Carboxylate, Sodium Pentaerythrityl Hydroxypropyl Iminodiacetate Dendrimer, Sodium Propoxy PPG-2 Acetate, Sodium Rapeseedate, Sodium Ricebranamphoacetate, Sodium Ricinoleate, Sodium Ricinoleoamphoacetate, Sodium Rose Hipsamphoacetate, Sodium Rosinate, Sodium Safflowerate, Sodium Safflowerоyl Hydrolyzed Soy Protein, Sodium Sesameseedate, Sodium Sesamphoacetate, Sodium Sheabutteramphoacetate, Sodium Soyate, Sodium Soy Hydrolyzed Collagen, Sodium Stearate, Sodium Stearoamphoacetate, Sodium Stearoamphohydroxypropylsulfonate, Sodium Stearoamphopropionate, Sodium Stearoyl Casein, Sodium Stearoyl Glutamate, Sodium Stearoyl Hyaluronate, Sodium Stearoyl Hydrolyzed Collagen, Sodium Stearoyl Hydrolyzed Corn Protein, Sodium Stearoyl Hydrolyzed Silk, Sodium Stearoyl Hydrolyzed Soy Protein, Sodium Stearoyl Hydrolyzed Wheat Protein, Sodium Stearoyl Lactalbumin, Sodium Stearoyl Methyl Isethionate, Sodium Stearoyl Oat Protein, Sodium Stearoyl Pea Protein, Sodium Stearoyl Soy Protein, Sodium Stearyl Dimethyl Glycine, Sodium Stearyl Sulfate, Sodium Sunflowerseedamphoacetate, Sodium Surfactin, Sodium Sweetalmondamphoacetate, Sodium Sweet Almondate, Sodium Tallamphopropionate, Sodium Tallate, Sodium Tallowamphoacetate, Sodium Tallowate, Sodium Tallow Sulfate, Sodium Tamanuseedate, Sodium Taurate, Sodium Taurine Cocoyl Methyltaurate, Sodium Taurine Laurate, Sodium/TEA-Lauroyl Collagen Amino Acids, Sodium/TEA-Lauroyl Hydrolyzed Collagen, Sodium/TEA-Lauroyl Hydrolyzed Keratin, Sodium/TEA-Lauroyl Keratin Amino Acids, Sodium/TEA-Undecylenoyl Collagen Amino Acids, Sodium/TEA-Undecylenoyl Hydrolyzed Collagen, Sodium/TEA-Undecylenoyl Hydrolyzed Corn Protein, Sodium/TEA-Undecylenoyl Hydrolyzed Soy Protein, Sodium/TEA-Undecylenoyl Hydrolyzed Wheat Protein, Sodium *Theobroma grandiflorum* Seedate, Sodium Trideceth-3 Carboxylate, Sodium Trideceth-4 Carboxylate, Sodium Trideceth-6 Carboxylate, Sodium Trideceth-7 Carboxylate, Sodium Trideceth-8 Carboxylate, Sodium Trideceth-12 Carboxylate, Sodium Trideceth-15 Carboxylate, Sodium Trideceth-19 Carboxylate, Sodium Trideceth Sulfate, Sodium Tridecylbenzenesulfonate, Sodium Tridecyl Sulfate, Sodium Trimethylolpropane Hydroxypropyl Iminodiacetate Dendrimer, Sodium Undeceth-5 Carboxylate, Sodium Undecylenate, Sodium Undecylenoamphoacetate, Sodium Undecylenoamphopropionate, Sodium Undecylenoyl Glutamate, Sodium Wheat Germamphoacetate, Sorbeth-160 Tristearate, Soy Acid, Soyamidopropylamine Oxide, Soyamidopropyl Betaine, Soybean Oil Glycereth-8 Esters, Stearamidopropylamine Oxide, Stearamidopropyl Betaine, Stearamine Oxide, Steareth-15, Steareth-16, Steareth-20, Steareth-21, Steareth-25, Steareth-27, Steareth-30, Steareth-40, Steareth-50, Steareth-80, Steareth-100, Steareth-2 Phosphate, Steareth-3 Phosphate, Stearic Acid, Stearoxypropyltrimonium Chloride, Stearoyl Glutamic Acid, Stearoyl Sarcosine, Stearyl Betaine, Stearyldimoniumhydroxypropyl Butylglucosides Chloride, Stearyldimoniumhydroxypropyl Decylglucosides Chloride, Stearyldimoniumhydroxypropyl Laurylglucosides Chloride, Sulfated Castor Oil, Sulfated Coconut Oil, Sulfated Glyceryl Oleate, Sulfated Olive Oil, Sulfated Peanut Oil, Sunfloweramide MEA, Sunflower Seed Acid, Sunflowerseedamidopropyl Hydroxyethyldimonium Chloride, Sunflower Seed Oil Glycereth-8 Esters, Tall Oil Acid, Tallow Acid, Tallowamidopropylamine Oxide, Tallowamidopropyl Betaine, Tallowamidopropyl Hydroxysultaine, Tallowamine Oxide, Tallow Betaine, Tallow Dihydroxyethyl Betaine, Tallowoyl Ethyl Glucoside, TEA-Abietoyl Hydrolyzed Collagen, TEA-C12-C14 Alkyl Phosphate, TEA-C10-C15 Alkyl Sulfate, TEA-C11-C15 Alkyl Sulfate, TEA-C12-C13 Alkyl Sulfate, TEA-C12-C14 Alkyl Sulfate, TEA-C12-C15 Alkyl Sulfate, TEA C14-C17 Alkyl Sec Sulfonate, TEA-Canolate, TEA-Cocamide Diacetate, TEA-Cocoate, TEA-Coco-Sulfate, TEA-Cocoyl Alaninate, TEA-Cocoyl Glutamate, TEA-Cocoyl Glutaminate, TEA-Cocoyl Glycinate, TEA-Cocoyl Hydrolyzed Collagen, TEA-Cocoyl Hydrolyzed Soy Protein, TEA-Cocoyl Sarcosinate, TEA-Dimethicone PEG-7 Phosphate, TEA-Dodecylbenzenesulfonate, TEA-Hydrogenated Cocoate, TEA-Hydrogenated Tallowoyl Glutamate, TEA-Isostearate, TEA-Isostearoyl Hydrolyzed Collagen, TEA-Lauraminopropionate, TEA-Laurate, TEA-Laurate/Myristate, TEA-Laureth Sulfate, TEA-Lauroyl Collagen Amino Acids, TEA-Lauroyl Glutamate, TEA-Lauroyl Hydrolyzed Collagen, TEA-Lauroyl Keratin Amino Acids, TEA-Lauroyl Methylaminopropionate, TEA-Lauroyl/Myristoyl Aspartate, TEA-Lauroyl Sarcosinate, TEA-Lauryl Phosphate, TEA-Lauryl Sulfate, TEA-Myristaminopropionate, TEA-Myristate, TEA-Myristoyl Hydrolyzed Collagen, TEA-Oleate, TEA-Oleoyl Hydrolyzed Collagen, TEA-Oleoyl Sarcosinate, TEA-Oleyl Sulfate, TEA-Palmitate, TEA-Palm Kernel Sarcosinate, TEA-PEG-3 Cocamide Sulfate, TEA-Rosinate, TEA-Stearate, TEA-Tallate, TEA-T ridecylbenzenesulfonate, TEA-Undecylenate, TEA-Undecylenoyl Hydrolyzed Collagen, Tetramethyl Decynediol, Tetrasodium Dicarboxyethyl Stearyl Sulfosuccinamate, TIPA-Laureth Sulfate, TIPA-Lauryl Sulfate, TIPA-Myristate, TIPA-Stearate, Tocopheryl Phosphate, Trehalose Undecylenoate, TM-C12-15 Pareth-2 Phosphate, TM-C12-15 Pareth-6 Phosphate, TM-C12-15 Pareth-8 Phosphate, TM-C12-15 Pareth-10 Phosphate, Trideceth-20, Trideceth-50, Trideceth-3 Carboxylic Acid, Trideceth-4 Carboxylic Acid, Trideceth-7 Carboxylic Acid, Trideceth-8 Carboxylic Acid, Trideceth-15 Carboxylic Acid, Trideceth-19 Carboxylic Acid, Trideceth-10 Phosphate, Tridecylbenzenesulfonic Acid, Trilaureth-9 Citrate, Trimethylolpropane Hydroxypropyl Bis-Hydroxyethylamine Dendrimer, Trisodium Lauroampho PG-Acetate Chloride Phosphate, Undecanoic Acid, Undeceth-5 Carboxylic Acid, Undecylenamidopropylamine Oxide, Undecylenamidopropyl Betaine, Undecylenic Acid, Undecylenoyl Collagen Amino Acids, Undecylenoyl Glycine, Undecylenoyl Hydrolyzed Collagen, Undecylenoyl Wheat Amino Acids, Undecyl Glucoside, Wheat Germ Acid, Wheat Germamidopropylamine Oxide, Wheat Germamidopropyl Betaine, *Yucca schidigera* Leaf/Root/Stem Extract, *Yucca schidigera* Stem Extract, Zinc Coceth Sulfatea and Zinc Coco-Sulfate, and mixtures of two or more of the afore-mentioned surfactants.

Preferred and typical examples for anionic or amphoteric or zwitterionic surfactants encompass behenamidopropyl betaine, behenyl betaine, betaine, betaine salicylate, capryl/capramidopropyl betaine, capryl sultaine, cetyl betaine, cocamidopropyl betaine cocamidopropyl hydroxysultaine, coco-betaine, coco-hydroxysultaine, decyl betaine, hydroxysultaines, lauramidopropyl betaine, lauramidopropyl hydroxysultaine, lauryl betaine, lauryl hydroxysultaine, lauryl sultaine, myristyl betaine, myristyl sultaine, oleyl betaine, palmamidopropyl betaine, palmitamidopropyl betaine, ricinoleamidopropyl betaine, soyamidopropyl betaine, stearamidopropyl betaine, stearyl betaine, tallowamidopropyl betaine, tallowamidopropyl hydroxysultaine, tallow betaine, and mixtures of two or more of said surfactants.

Preferably, most preferably for a shampoo formulation, the at least one surfactant is selected from the group of anionic or amphoteric or zwitterionic surfactant consisting of ammonium lauryl sulfosuccinate, sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, sodium lauroyl sarcosinate, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, cocamide-MEA, PEG-7 glyceryl cocoate, glycol/distearate, sodium oleoyl sarcosinate, sodium cocoyl isethionate, sodium cocoamphoacetate, sodium cocoyl glutamate, sodium methyl cocoyl taurate, and mixtures of two or more of the afore-mentioned surfactants.

The use of a combination of anionic and/or amphoteric surfactants with one or more non-ionic surfactants is also advantageous.

Other non-ionic or cationic surfactants may also be added to the surfactant containing formulation, including for example:

- products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated C6/22 fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred surfactants are described in more detail as follows:

Partial glycerides: Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters: Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters: Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Poly-glyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Tetraalkyl ammonium salts: Cationically active surfactants comprise the hydrophobic high molecular group required for the surface activity in the cation by dissociation in aqueous solution. A group of important representatives of the cationic surfactants are the tetraalkyl ammonium salts of the general formula: $(R^1R^2R^3R^4N^+)\ X^-$. Here R1 stands for $C_1$-$C_8$ alk(en)yl, $R^2$, $R^3$ and $R^4$, independently of each other, for alk(en)yl radicals having 1 to 22 carbon atoms. X is a counter ion, preferably selected from the group of the halides, alkyl sulfates and alkyl carbonates. Cationic surfactants, in which the nitrogen group is substituted by two long acyl groups and two short alk(en)yl groups, are particularly preferred.

Esterquats: A further class of cationic surfactants particularly useful as co-surfactants for the present invention is represented by the so-called esterquats. Esterquats are generally understood to be quaternised fatty acid triethanolamine ester salts. These are known compounds which can be obtained by the relevant methods of preparative organic chemistry. Reference is made in this connection to International patent application WO 91/01295 A1, according to which triethanolamine is partly esterified with fatty acids in the presence of hypophosphorous acid, air is passed through the reaction mixture and the whole is then quaternised with dimethyl sulphate or ethylene oxide. In addition, German patent DE 4308794 C1 describes a process for the production of solid esterquats in which the quaternisation of triethanolamine esters is carried out in the presence of suitable dispersants, preferably fatty alcohols. Typical examples of esterquats suitable for use in accordance with the invention are products of which the acyl component derives from monocarboxylic acids corresponding to formula RCOOH in which RCO is an acyl group containing 6 to 10 carbon atoms, and the amine component is triethanolamine (TEA). Examples of such monocarboxylic acids are caproic acid, caprylic acid, capric acid and technical mixtures thereof such as, for example, so-called headfractionated fatty acid. Esterquats of which the acyl component derives from monocarboxylic acids containing 8 to 10 carbon atoms, are preferably used. Other esterquats are those of which the acyl component derives from dicarboxylic acids like malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component derives from mixtures of monocarboxylic acids containing 6 to 22 carbon atoms, and adipic acid are preferably used. The molar ratio of mono and dicarboxylic acids in the final esterquat may be in the range from 1:99 to 99:1 and is preferably in the range from 50:50 to 90:10 and more particularly in the range from 70:30 to 80:20. Besides the quaternised fatty acid triethanolamine ester salts, other suitable esterquats are quaternized ester salts of mono-/dicarboxylic acid mixtures with diethanolalkyamines or 1,2-dihydroxypropyl dialkylamines. The esterquats may be obtained both from fatty acids and from the corresponding triglycerides in admixture with the corresponding dicarboxylic acids. One such process, which is intended to be representative of the relevant prior art, is proposed in European patent EP 0750606 B1. To produce the quaternised esters, the mixtures of mono- and dicarboxylic acids and the triethanolamine—based on the available carboxyl functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9.

Compound (a) according to the present invention, namely the surfactant, is present in the surfactant containing formulation according to the present invention, preferably in the cosmetic or pharmaceutical, in particular dermatological, formulation, in an amount of at least 5% by weight or higher, based on the total weight of the formulation. In a preferred variant, the surfactant containing formulation comprises the surfactant in an amount of at least 7% by weight or higher, based on the total weight of the formulation. In a particular preferred variant, the surfactant is advantageously used in the surfactant containing formulation in an amount of at least 10% by weight or higher and up to 20 to 90% by weight in highly concentrated systems, such as solid formulations. In concentrated surfactant containing formulations, preferably in liquid ready-for-use products, the surfactant content is preferably in a range from 5 to 30% by weight, based on the total weight of the formulation. In concentrated surfactant containing formulations, preferably in solid ready-for-use products, the surfactant content is preferably in a range from 30 to 60% by weight, based on the total weight of the formulation.

By contrast, customarily a cosmetic formulation in emulsion form such as lotion, dispersion, suspension, cream, lotion or milk, ointment, paste, gel etc. contains a surfactant for emulsification in a considerably lower amount, i.e. in an amount lower than 5% by weight, in particular 1 to 3% by weight, based on the total weight of the cosmetic preparation. Thus, such emulsions are not a surfactant containing formulation in accordance with the definition of the present invention.

The second component (b) of the surfactant containing formulation according to the first aspect of the present invention is an N-acyl hydroxy amino acid ester represented by the general formula (I)

Formula (I)

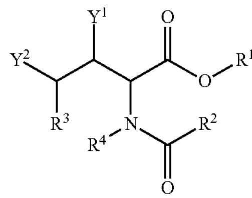

or an enantiomer thereof.

In the general Formula (I)

R1 is a linear, branched or cyclic alkyl or alkenyl group having 5 to 50 carbon atoms and optionally substituted by one or more hydroxyl group(s), preferably a linear, branched or cyclic alkyl or alkenyl group having 5 to 24 carbon atoms and optionally substituted by 1 to 6 hydroxyl group(s), R2 is a linear or branched alkyl or alkenyl group having 1 to 49 carbon atoms and optionally substituted by one or more hydroxyl group(s), preferably a linear or branched alkyl or alkenyl group having 2 to 23 carbon atoms and optionally substituted by 1 to 6 hydroxyl group(s), more preferred a linear or branched alkyl or alkenyl group having 2 to 23 carbon atoms and optionally substituted by 1 to 3 hydroxyl group(s), Y1 and Y2 are independently of one another, hydrogen or a hydroxyl group, preferably only one of the two groups Y1 and Y2 is a hydroxyl group and the other is a hydrogen atom, R3 and R4 are either independently of one another, hydrogen or a linear or branched alkyl or alkenyl group having 1 to 10 carbon atoms, preferably hydrogen or a linear or branched alkyl or alkenyl group having 1 to 4 carbon atoms, more preferred hydrogen, methyl or ethyl, especially hydrogen, or R3 and R4 together are an alkyl group having 1 to 3 carbon atoms or together with the chain between R3 and R4 form a 5- to 7-membered heterocyclic ring, wherein the alkyl group is optionally substituted by 1 to 3 linear or branched alkyl or alkenyl group(s) or is substituted by 1 to 3 hydroxyl group(s).

In a preferred variant of the general Formula (I), R1 and/or R2 represent a linear or branched alkyl or alkenyl group having 10 to 20 carbon atoms, optionally substituted by 1 to 3 hydroxyl group(s).

In a more preferred variant of the general Formula (I), one of the two Y1 or Y2 is a hydroxyl group and the other is hydrogen. Preferably Y2 is a hydroxyl group.

In an even more preferred variant of the general Formula (I), either R3 and R4 independently of each other are hydrogen or a linear or branched alkyl or alkenyl group having 1, 2, 3 or 4 carbon atoms, or R3 and R4 together are $—CH_2—$, $—CH_2—CH_2—$, —CH(OH)—, $—CH(OH)—CH_2—$ or $CH_2—CH(OH)—$, in order to form a closed heterocyclic ring.

In particular, N-acyl hydroxyamino acid esters according to the general Formula (I) are preferably used according to the invention, wherein R1 and R2 are as defined above and either R3 and R4 each are hydrogen and Y1 and Y2 independently of one another each are hydrogen or a hydroxyl group, or R3 and R4 together are $—CH_2—$ or —CH(OH)— and together with the chain between R3 and R4 form a 5-membered heterocyclic ring, and at the same time Y1 and Y2 independently of one another each are hydrogen or a hydroxyl group.

According to the invention, N-acyl hydroxy amino acid esters according to the general Formula (I) are used even more preferably, wherein R1 and R2 are as defined above and R3 and R4 each are hydrogen and Y1 and Y2 independently of one another each are hydrogen or a hydroxyl group, even more preferably Y2 represents a hydroxyl group and Y1 is hydrogen, and R3 and R4 together is $—CH_2—$ and together with the chain between R3 and R4 form a 5-membered heterocyclic ring and one of the two Y1 and Y2 is a hydroxyl group.

In an even more preferred variant of the general Formula (I), R1 represents a linear alkyl or alkenyl group having 5 to 24 carbon atoms and R2 represents a linear alkyl or alkenyl group having 2 to 23 carbon atoms.

Preferably, in the general Formula (I), R1 is a linear alkyl chain with 14 to 18 carbon atoms, more preferably a linear alkyl chain with 16 carbon atoms, and R2 is preferably a linear alkyl chain with 13 to 18 carbon atoms, more preferably a linear alkyl chain with 15 carbon atoms. Such compounds show particularly strong effects.

Most preferably, the N-acyl hydroxyamino acid ester represented by the general Formula (I) is an N-acyl hydroxyamino acid ester as represented by the formula (II)

Formula (II)

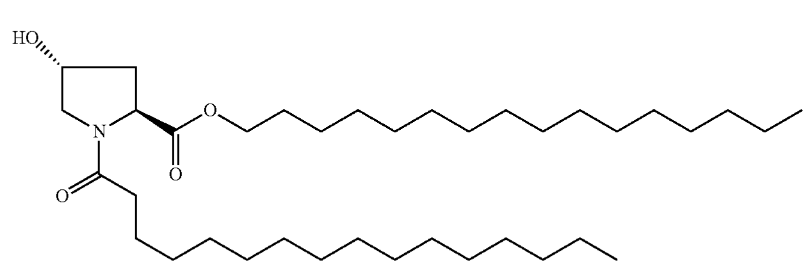

or an enantiomer thereof.

The N-acyl hydroxyamino acid esters of the general formula (I) or the N-acyl hydroxyamino acid ester of the formula (II), in a further variant according to the first aspect of the present invention, also comprise their enantiomers. In particular, the N-acyl hydroxyamino acid esters of general formula (I) are preferably used, which are present in the following forms: in a first variant, the compound is present as a pure optically active enantiomer; in an alternative variant, the compound is present as a racemic mixture of the enantiomers, or further in an optically active mixture of different enantiomers.

In a preferred variant of the present invention, the surfactant containing formulation may comprise a mixture of two or more of the N-acyl hydroxyamino acid esters of the general Formula (I). In a more preferred variant of the present invention, the surfactant containing formulation comprises at least one N-acyl hydroxyamino acid ester of the general Formula (I). In a particularly preferred variant of the present invention, the surfactant containing formulation comprises the N-acyl hydroxyamino acid ester according to the Formula (II).

The N-acyl hydroxy amino acid esters according to the general Formula (I) or the specific N-acyl hydroxyl amino ester of the Formula (II) or their enantiomer(s) are analogous structures of naturally occurring ceramides, so-called "synthetic barrier lipids (SBL)" or "pseudoceramides". They have a low melting range of 56 to 59° C.

In particular, the N-acyl hydroxyl amino acid ester according to the formula (II) is a pseudoceramide resembling natural Ceramide 2 activity.

The N-acyl hydroxy amino acid esters used in accordance with the invention are colourless or slightly ivory-coloured, odourless substances which can be homogeneously incorporated into the oil phase of cosmetic or pharmaceutical, in particular dermatological, preparations.

The surfactant containing formulation according to the first aspect of the present invention comprises the N-acyl hydroxy amino acid ester Surprisingly, it was found, as described in more detail in the following examples, that the N-acyl hydroxy amino acid esters according to the general formula (I) and in particular the N-acyl hydroxy amino acid ester according to formula (II) are easy to incorporate into a surfactant containing formulation, due to their low melting range. Additionally, the N-acyl hydroxyl amino acid esters show an excellent solubility in a surfactant containing formulation. The solubility of the N-acyl hydroxy amino acid esters according to the general formula (I) and in particular the N-acyl hydroxyl amino acid according to formula (II) in surfactant containing formulations is better compared to the solubility of Ceramide 2 or Ceramide 3 in surfactant containing formulations, as it is demonstrated by the following examples. Due to their excellent solubility in a surfactant containing formulation, the pseudoceramides as defined above and as used according to the present invention, in particular the pseudoceramide according to formula (II), can be advantageously provided in high concentrations in the surfactant containing formulation. This in turn enhances the bioavailability of the pseudoceramide in the target, for strengthening the barrier function of the skin, hair, scalp and nails, to maintain intact skin, hair, scalp and nails, improve the water retention capacity of the stratum corneum as well as to support the repair of damaged skin, hair, scalp and nails.

Additionally, the pseudoceramide according to the general Formula (I) and in particular the pseudoceramide according to the Formula (II) is stable in the surfactant containing formulation, which is an important factor for the shelf life of the surfactant containing formulation, i.e. any consumer formulations, according to the present invention.

Furthermore, the pseudoceramide according to the general Formula (I) and in particular the pseudoceramide according to Formula (II) does not precipitate in the surfactant containing formulation and thus, does not result in a turbidity, in particular in liquid surfactant containing formulations.

The pseudoceramide according to the general Formula (I) and in particular the pseudoceramide according to Formula (II) is advantageously used in the surfactant containing formulation, for example in a shampoo, leave-on conditioner, etc., according to the present invention in an amount from 0.001 to 1.0% by weight, based on the total amount of the surfactant containing formulation. Preferably, said pseudoceramide is used in the surfactant containing formulation in an amount from 0.005 to 0.5% by weight, based on the total amount of the surfactant containing formulation. If the amount of the pseudoceramide in the formulation exceeds 1% by weight, there is the disadvantage that the foam generation and the cleansing power decreases.

Within the context of the present invention, it is also possible—and in some cases advantageous—to combine the surfactant containing formulation, preferably a cosmetic or pharmaceutical formulation, according to the present invention with other active agents.

Optionally, other conventional cosmetically and/or dermatologically active substances or additives, as further described below, may be added to the surfactant containing formulation according to the invention as component (c), i.e. in order to obtain a ready-for-use formulation.

The surfactant containing formulation, preferably a cosmetic or pharmaceutical formulation, according to the present invention can advantageously be combined with other cosmetically or pharmaceutically active agents and/or additives or auxiliaries, such as are customarily used in such formulations, such as for example antioxidants, perfume oils, anti-foaming agents, colorants, pigments having a colouring action, thickeners, surface-active substances, emulsifiers, plasticising substances, moistening and/or moisture-retaining substances, fats, oils, waxes or other conventional constituents of a cosmetic or pharmaceutical preparation, such as alcohols, polyols, polymers, foam stabilisers, electrolytes, organic solvents or silicone derivatives. Any conceivable antioxidants, perfume oils, anti-foaming agents, colorants, pigments having a colouring action, thickeners, surface-active substances, emulsifiers, plasticising substances, moistening and/or moisture-retaining substances, fats, oils, waxes, alcohols, polyols, polymers, foam stabilisers, electrolytes, organic solvents or silicone derivatives that are suitable or customary in cosmetic or pharmaceutical applications, and/or cosmetically or pharmaceutically acceptable excipients, as in detail described and exemplified below.

In a particularly preferred variant of the present invention, the surfactant containing formulation advantageously contains (alpha-)bisobolol and phytosterols. Such a combination mimic the "motar" in the stratum corneum therefore strengthen the barrier of the skin, hair, scalp and nails.

Since dermatological conditions or diseases are often associated with dry skin, scratched skin, skin lesions or even inflammation, the surfactant containing formulation, preferably a cosmetic or pharmaceutical formulation, according to the present invention particularly advantageously contains preferably anti-inflammatories, antibacterial or antimycotic substances, substances having a reddening-alleviating or itch-alleviating action, lenitive substances, moisturisers and/or cooling agents, osmolytes, keratolytic substances, nurturing substances, anti-inflammatory, antibacterial or antimycotic substances, substances having a reddening-alleviating or itch-alleviating action, lenitive substances, antidandruff substances, or other active compounds such as solvents, fragrances antioxidants, preservatives, (metal) chelating agents, penetration enhancersor, or mixtures of two or more of afore-specified agents.

Itching occurs with particular intensity when the skin is dry. The use of skin-moisturising and/or moisture-retaining substances can significantly alleviate itching. The surfactant containing formulation, preferably a cosmetic or pharmaceutical formulation, according to the present invention can therefore advantageously also contain the following moisturising and/or moisture-retaining substances: sodium lactate, urea, urea derivatives, alcohols, glycerol, diols such as propylene glycol, hexylene glycol, 1,2-pentanediol, 1,2-hexanediol, 1,2-heptanediol, 1,2-octanediol, 1,2-nonanediol, 1,2-decanediol or mixtures of said diols, in particular mixtures of 1,2-hexanediol and 1,2-octanediol, collagen, elastin or hyaluronic acid, diacyl adipates, petrolatum, urocanic acid, lecithin, panthenol, phytantriol, lycopene, (pseudo-)ceramides, glycosphingolipids, cholesterol, phytosterols, chitosan, chondroitin sulphate, lanolin, lanolin esters, amino acids, alpha-hydroxy acids (such as citric acid, lactic acid, malic acid) and their derivatives, mono-, di- and oligosaccharides such as glucose, galactose, fructose, mannose, fructose and lactose, polysugars such as R-glucans, in particular 1,3-1,4-β-glucan from oats, alpha-hydroxy fatty acids, triterpene acids such as betulinic acid or ursolic acid, and algae extracts.

The use of cooling agents can alleviate itching. The surfactant containing formulation, preferably a cosmetic or pharmaceutical formulation, according to the present invention can therefore also be particularly advantageously combined with one or more cooling agent(s). Preferred individual cooling agents for use within the framework of the present invention are listed below. The person skilled in the art can add many other cooling agents to this list; the cooling agents listed can also be used in combination with one another: l-menthol, d-menthol, racemic menthol, menthone glycerol acetal (trade name: Frescolat® MGA), menthyl lactate (trade name: Frescolat® ML; menthyl lactate is preferably l-menthyl lactate, in particular l-menthyl l-lactate), substituted menthyl-3-carboxamides (such as menthyl-3-carboxylic acid N-ethyl amide), 2-isopropyl-N-2,3-trimethyl butanamide, substituted cyclohexane carboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (such as menthyl 3-hydroxybutyrate), monomenthyl succinate, 2-mercaptocyclodecanone, menthyl 2-pyrrolidin-5-one carboxylate, 2,3-dihydroxy-p-menthane, 3,3,5-trimethyl cyclohexanone glycerol ketal, 3-menthyl-3,6-di- and trioxaalkanoates, 3-menthyl methoxyacetate and icilin.

Cooling agents which are preferred due to their particular synergistic effect are l-menthol, d-menthol, racemic menthol, menthone glycerol acetal (trade name: Frescolat® MGA), menthyl lactate (preferably l-menthyl lactate, in particular l-menthyl l-lactate (trade name: Frescolat® ML)), substituted menthyl-3-carboxamides (such as menthyl-3-carboxylic acid N-ethyl amide), 2-isopropyl-N-2,3-trimethyl butanamide, substituted cyclohexane carboxamides, 3-menthoxypropane-1,2-diol, 2-hydroxyethyl menthyl carbonate, 2-hydroxypropyl menthyl carbonate and isopulegol.

Particularly preferred cooling agents are l-menthol, racemic menthol, menthone glycerol acetal (trade name: Frescolat® MGA), menthyl lactate (preferably l-menthyl lactate, in particular l-menthyl l-lactate (trade name: Frescolat® ML)), 3-menthoxypropane-1,2-diol, 2-hydroxyethyl menthyl carbonate and 2-hydroxypropyl menthyl carbonate. Very particularly preferred cooling agents are l-menthol, menthone glycerol acetal (trade name: Frescolat® MGA) and menthyl lactate (preferably l-menthyl lactate, in particular l-menthyl l-lactate (trade name: Frescolat® ML).

The surfactant containing formulation, preferably a cosmetic or pharmaceutical formulation, according to the present invention can also contain one or more osmolyte(s). Examples of osmolytes which may be mentioned here include substances from the group comprising sugar alcohols (myoinositol, mannitol, sorbitol), quaternary amines such as taurine, choline, betaine, betaine glycine, ectoin, diglycerol phosphate, phosphorylcholine or glycerophosphorylcholines, amino acids such as glutamine, glycine, alanine, glutamate, aspartate or proline, phosphatidylcholine, phosphatidylinositol, inorganic phosphates, and polymers of said compounds, such as proteins, peptides, polyamino acids and polyols. All osmolytes simultaneously have a skin-moisturising action.

Preferably, keratolytic substances can also be combined with the surfactant containing formulation according to the present invention. Keratolytic compounds include the large group of alpha-hydroxy acids. Salicylic acid is for example preferably used.

In the surfactant containing formulation, preferably a cosmetic or pharmaceutical formulation, according to the present invention a high proportion of in particular nurturing substances is also particularly advantageous because of the reduced trans-epidermal water loss due to lipophilic components. In one preferred embodiment, the cosmetic or pharmaceutical, in particular dermatological, formulation contain one or more nurturing animal and/or vegetable fats and oils such as olive oil, sunflower oil, refined soybean oil, palm oil, sesame oil, rapeseed oil, almond oil, borage oil, evening primrose oil, coconut oil, shea butter, jojoba oil, sperm oil, tallow, neatsfoot oil and lard, and optionally other nurturing components such as fatty alcohols having 8 to 30 C atoms. The fatty alcohols used here can be either saturated or unsaturated and either linear or branched. Nurturing substances which can be particularly preferably combined with the mixtures according to the present invention also include in particular ceramides, understood here to mean N-acylsphingosines (fatty acid amides of sphingosine) or synthetic analogues of such lipids (so-called pseudoceramides) which markedly improve the water retention capacity of the stratum corneum; phospholipids, such as soy lecithin, egg lecithin and cephalins; and petrolatum, paraffin oils and silicone oils, the latter including inter alia dialkyl- and alkylarylsiloxanes such as dimethylpolysiloxane and methylphenylpolysiloxane and their alkoxylated and quaternised derivatives.

The surfactant containing formulation, preferably a cosmetic or pharmaceutical formulation, according to the present invention can also contain one or more anti-inflammatory substances. Advantageously, the anti-inflammatory active compounds are steroidal anti-inflammatory substances of the corticosteroid type, such as for example hydrocortisone, dexamethasone, dexamethasone phosphate, methylprednisolone or cortisone, wherein this list may be expanded by adding other steroidal anti-inflammatory agents. Non-steroidal anti-inflammatory agents can also be used, for example: oxicams, such as piroxicam or tenoxicam; salicylates, such as aspirin, Disalcid®, Solprin® or fendosal; acetic acid derivatives, such as diclofenac, fenclofenac, indomethacin, sulindac, tolmetin or clindanac; fenamates, such as mefenamic, meclofenamic, flufenamic or niflumic acid; propionic acid derivatives, such as ibuprofen, naproxen, benoxaprofen; or pyrazoles, such as phenylbutazone, oxyphenylbutazone, febrazone or azapropazone. Alternatively, natural anti-inflammatory substances can be used.

Plant extracts, special highly active plant extract fractions and also highly pure active substances isolated from plant extracts can also be used in the surfactant containing formulation, preferably a cosmetic or pharmaceutical formulation, according to the present invention. Extracts, fractions and active substances from camomile, aloe vera, *Commiphora* species, *Rubia* species, willows, willow-herb, ginger, marigold, *arnica, Glycyrrhiza* species, *Echinacea* species, *Rubus* species and pure substances such as inter alia bisabolol, apigenin, apigenin-7-glucoside, gingerols such as [6]-gingerol, paradols such as [6]-paradol, boswellic acid, phytosterols, glycyrrhizine, glabridin or licochalcone A are particularly preferred.

The surfactant containing formulation, preferably a cosmetic or pharmaceutical formulation, according to the present invention can also contain active compounds for preservative purposes, wherein any preservatives may be used which are suitable or customary in cosmetic or pharmaceutical, in particular dermatological, applications and which are advantageously selected from the group consisting of preservatives such as inter alia benzoic acid, its esters and salts; propionic acid and its salts; salicylic acid and its salts; 2,4-hexanoic acid (sorbic acid) and its salts; formaldehyde and paraformaldehyde; 2-hydroxybiphenyl ether and its salts; 2-zincsulphidopyridine N-oxide; inorganic sulphites and bisulphites; sodium iodate; chlorobutanol; 4-hydroxybenzoic acid and its salts and esters; dehydroacetic acid; formic acid; 1,6-bis(4-amidino-2-bromophenoxy)-n-hexane and its salts; the sodium salt of ethylmercury-(II)-thiosalicylic acid; phenylmercury and its salts; 10-undecylenic acid and its salts; 5-amino-1,3-bis(2-ethylhexyl)-5-methylhexahydropyrimidine; 5-bromo-5-nitro-1,3-dioxane; 2-bromo-2-nitro-1,3-propanediol; 2,4-dichlorobenzyl alcohol; N-(4-chlorophenyl)-N'-(3,4-dichlorophenyl)urea; 4-chloro-m-cresol; 2,4,4'-trichloro-2'-hydroxy-diphenyl ether; 4-chloro-3,5-dimethylphenol; 1,1'-methylene-bis(3-(1-hydroxymethyl-2,4-dioximidazolidin-5-yl)urea); poly (hexamethylene biguanide) hydrochloride; 2-phenoxyethanol; hexamethylenetetramine; 1-(3-chloroallyl)-3,5,7-triaza-1-azoniaadamantane chloride; 1-(4-chlorophenoxy)-1(1H-imidazol-1-yl)-3,3-dimethyl-2-butanone; 1,3-bis(hydroxymethyl)-5,5-dimethyl-2,4-imidazolidinedione; benzyl alcohol; Octopirox®; 1,2-dibromo-2,4-dicyanobutane; 2,2'-methylene-bis(6-bromo-4-chloro-phenol); bromochlorophene; mixture of 5-chloro-2-methyl-3 (2H)-isothiazolinone and 2-methyl-3(2H)isothiazolinone with magnesium chloride and magnesium nitrate; 2-benzyl-4-chlorophenol; 2-chloroacetamide; chlorhexidine; chlorhexidine acetate; chlorhexidine gluconate; chlorhexidine hydrochloride; 1-phenoxy-propan-2-ol; N-alkyl(C12-C22) trimethylammonium bromide and chloride; 4,4-dimethyl-1,3-oxazolidine; N-hydroxymethyl-N-(1,3-di(hydroxymethyl)-2,5-dioxoimidazolidin-4-yl)-N'-hydroxymethylurea; 1,6-bis(4-amidinophenoxy)-n-hexane and its salts; glutaraldehyde 5-ethyl-1-aza-3,7-dioxabicyclo(3.3.0)octane; 3-(4-chlorophenoxy)-1,2-propanediol; hyamine; alkyl(C8-C18) dimethylbenzylammonium chloride; alkyl(C8-C18) dimethylbenzylammonium bromide; alkyl(C8-C18) dimethylbenzylammonium saccharinate; benzylhemiformal; 3-iodo-2-propynyl butylcarbamate; or sodium ((hydroxymethyl)amino)acetate.

Other antibacterial or antimycotic active substances can also particularly advantageously be used in the surfactant containing formulation, preferably a cosmetic or pharmaceutical formulation, according to the present invention, wherein any antibacterial or antimycotic active substances can be used which are suitable or customary in cosmetic or pharmaceutical, in particular dermatological applications. In addition to the large group of conventional antibiotics, other products which are advantageous here include those relevant to cosmetics such as in particular triclosan, climbazole, octoxyglycerin, Octopirox® (1-hydroxy-4-methyl-6-(2,4,4-trimethylpentyl)-2(1H)-pyridone 2-aminoethanol salt), chitosan, farnesol, glycerol monolaurate or combinations of said substances, which are used inter alia against underarm odour, foot odour or dandruff.

The surfactant containing formulation, preferably a cosmetic or pharmaceutical formulation, according to the present invention can also contain one or more lenitive substances, wherein any lenitive substances can be used which are suitable or customary in cosmetic or pharmaceutical applications such as alpha-bisabolol, azulene, guaiazulene, 18-beta-glycyrrhetinic acid, allantoin, Aloe vera juice or gel, extracts of *Hamamelis virginiana* (witch hazel), *Echinacea* species, *Centella asiatica*, chamomile, *Arnica montana, Glycyrrhiza* species, algae, seaweed and *Calendula officinalis*, and vegetable oils such as sweet almond oil, baobab oil, olive oil and panthenol, Laureth-9, Trideceth-9 and 4-t-butylcyclohexanol.

In addition, the surfactant containing formulation, preferably a cosmetic or pharmaceutical formulation, according to the present invention can also particularly advantageously be used in combination with one or more antidandruff substance, including triclosan, climbazole, octoxyglycerin, Octopirox® (1-hydroxy-4-methyl-6-(2,4,4-trimethylpentyl)-2(1H)-pyridone 2-aminoethanol salt), chitosan, farnesol, glycerol monolaurate, Propanedio Monocaprylate or combinations of said substances, which are used inter alia against underarm odour, foot odour or dandruff.

In addition, the surfactant containing formulation, preferably a cosmetic or pharmaceutical formulation, according to the present invention can also particularly advantageously be used in combination with one or more perspiration-inhibiting active compounds (antiperspirants) for controlling body odour. Perspiration-inhibiting active compounds used include in particular aluminium salts, such as aluminium chloride, chlorohydrate, nitrate, sulphate, acetate, etc. The use of zinc, magnesium or zirconium compounds can however also be advantageous. Aluminium salts and, to a somewhat lesser extent, aluminium/zirconium salt combinations have proven useful as cosmetic or pharmaceutical antiperspirants. Partially neutralised aluminium hydroxychlorides, which are therefore more tolerable to the skin but are not quite as effective, are also noteworthy. Substances other than aluminium salts can also be used, such as for example: (a) protein-precipitating substances such as inter alia formaldehyde, glutaraldehyde, natural and synthetic tanning agents and trichloroacetic acid, which cause surface closure of the sweat glands; (b) local anaesthetics, including dilute solutions of for example lidocaine, prilocaine or mixtures of the same, which switch off the sympathetic supply to the sweat glands by blocking the peripheral nerve paths; (c) zeolites of the X, A or Y type, which reduce sweat secretion and also act as adsorbents for bad odours; and (d) botulinus toxin (the toxin of the bacterium *Chlostridium botulinum*), which is also used in hyperhidrosis (pathological increase in sweat secretion), and the action of which is based on irreversibly blocking the release of the transmitter substance acetylcholine which is relevant to sweat secretion.

A combination with (metal) chelating agents can also be advantageous used in the surfactant containing formulation, preferably a cosmetic or pharmaceutical formulation, according to the present invention, wherein any metal chelating agents can be used which are suitable or customary in cosmetic or pharmaceutical applications. Preferred (metal) chelating agents include α-hydroxy fatty acids, phytic acid, lactoferrin, α-hydroxy acids, such as inter alia gluconic acid, glyceric acid, glycolic acid, isocitric acid, citric acid, lactic acid, malic acid, mandelic acid, tartaric acid, as well as humic acids, bile acids, bile extracts, bilirubin, biliverdin or EDTA, EGTA and their derivatives. The use of one or more chelating agent(s) improves the stability of the surfactant containing formulation according to the present invention.

The surfactant containing formulation, preferably a cosmetic or pharmaceutical formulation, according to the present invention can advantageously be combined with one or more substances that absorb UV radiation in the UVB range in order to provide cosmetic preparations that protect the hair and/or skin against the entire range of ultraviolet radiation. They can also serve as sunscreens for hair. If the preparations according to the present invention contain UVB filter substances, these can be oil-soluble or water-soluble. Advantageous oil-soluble UVB filters include: 3-benzylidene camphor derivatives, preferably 3-(4-methylbenzylidene)camphor, 3-benzylidenecamphor; 4-aminobenzoic acid derivatives, preferably 2-ethylhexyl 4-(dimethylamino) benzoate, amyl 4-(dimethylamino)benzoate; esters of cinnamic acid, preferably 2-ethylhexyl 4-methoxycinnamate, isopentyl 4-methoxycinnamate; esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di(2-ethylhexyl) 4-methoxybenzalmalonate, 2,4,6-trianilino-(p-carbo-2'-ethyl-1'-hexyloxy)-1,3,5-triazine. Advantageous water-soluble UVB filters include salts of 2-phenylbenzimidazole-5-sulphonic acid, such as its sodium, potassium or triethanolammonium salts, as well as the sulphonic acid itself; sulphonic acid derivatives of benzophenones, preferably 2-hydroxy-4-methoxybenzophenone-5-sulphonic acid and its salts; sulphonic acid derivatives of 3-benzylidene camphor, such as for example 4-(2-oxo-3-bornylidenemethyl)benzenesulphonic acid, 2-methyl-5-(2-oxo-3-bornylidene-methyl)sulphonic acid and their salts and also 1,4-di(2-oxo-10-sulpho-3-bornylidenemethyl)-benzene and its salts (the corresponding 10-sulphato compounds, such as the corresponding sodium, potassium and triethanolammonium salts), and benzene-1,4-di(2-oxo-3-bornylidenemethyl-10-sulphonic acid.

It can also be advantageous to employ one or more UVA filters, such as are customarily contained in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The amounts used for the UVB combination can be used analogously.

A high content of treatment substances is usually advantageous in the surfactant containing formulation according to the present invention for the cosmetic treatment of the skin, hair, scalp or nails. In accordance with a preferred embodiment, the surfactant containing formulations according to the present invention contain one or more animal and/or vegetable treatment fats and oils, such as olive oil, sunflower oil, purified soybean oil, palm oil, sesame oil, rapeseed oil, almond oil, borage oil, evening primrose oil, coconut oil, shea butter, jojoba oil, sperm oil, beef tallow, neatsfoot oil and lard, and optionally other treatment constituents such as for example C8- to C30 fatty alcohols. The fatty alcohols used here can be saturated or unsaturated and straight-chain or branched, wherein examples include decanol, decenol, octanol, octenol, dodecanol, dodecenol, octadienol, decadienol, dodecadienol, oleyl alcohol, ricinoleyl alcohol, erucic alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well their guerbet alcohols; this list may be extended as desired to include other alcohols which structurally are chemically related. The fatty alcohols preferably originate from natural fatty acids and are usually prepared from the corresponding esters of the fatty acids by reduction. Fatty alcohol fractions formed by reduction from naturally occurring fats and fat oils can also be used, such as for example beef tallow, peanut oil, colza oil, cottonseed oil, soybean oil, sunflower oil, palm kernel oil, linseed oil, maize oil, castor oil, rapeseed oil, sesame oil, cocoa butter and cocoa fat. The treatment substances that can preferably be combined with the surfactant containing formulation according to the present invention can also include: phospholipids, for example soy lecithin, egg lecithin and cephalins; vaseline, paraffin and silicone oils, the latter including inter alia dialkyl- and alkylarylsiloxanes such as dimethylpolysiloxane and methylphenylpolysiloxane, as well as their alkoxylated and quaternised derivatives.

Hydrolysed animal and/or vegetable proteins can also advantageously be added to the surfactant containing formulation according to the present invention. Advantageous examples in this regard include in particular elastin, collagen, keratin, lactoprotein, soy protein, oat protein, pea protein, almond protein and wheat protein fractions or corresponding hydrolysed proteins, as well as their condensation products with fatty acids, and also quaternised hydrolysed proteins, wherein the use of hydrolysed vegetable proteins is preferred.

If the surfactant containing formulation according to the present invention is a solution or lotion, then solvents which can be used include: water or aqueous solutions; fatty oils, fats, waxes and other natural and synthetic fatty bodies, preferably esters of fatty acids with alcohols having a low C number, such as isopropanol, propylene glycol or glycerol, or esters of fatty alcohols with alkanoic acids having a low C number or with fatty acids; alcohols, diols or polyols having a low C number, and their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products. Mixtures of the abovementioned solvents are in particular used. In the case of alcoholic solvents, water can be an additional constituent.

The surfactant containing formulation, preferably a cosmetic or pharmaceutical formulation, according to the present invention can also contain one or more antioxidants, wherein any antioxidants suitable or customary in cosmetic or pharmaceutical applications can be used. Advantageously, the antioxidants are selected from the group consisting of amino acids (for example glycine, histidine, tyrosine, tryptophan) and their derivatives, imidazoles (for example urocanic acid) and their derivatives, peptides such as D,L-carnosine, D-carnosine, L-carnosine and their derivatives (for example anserine), carotenoids, carotenes (for example α-carotene, β-carotene, lycopene) and their derivatives, lipoic acid and its derivatives (for example dihydrolipoic acid), aurothioglucose, propylthiouracil and other thiols (for example thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and their derivatives (esters, ethers, peptides, lipids, nucleotides, nucleosides and salts) as well as sulphoximine compounds (for example buthionine sulphoximines, homocysteine sulphoximines, buthionine sulphones, penta-, hexa-, hepta-thionine sulphoximine) in very low tolerated doses, and also (metal) chelating agents, for example α-hydroxy fatty acids, palmitic acid, phytic acid, lactoferrin, α-hydroxy acids (for example citric acid, lactic acid, malic acid), humic acid, bile acid, bile extracts, bilirubin, biliverdin, EDTA, EGTA and their derivatives, unsaturated fatty acids and their derivatives (for example γ-linolenic acid, linoleic acid, oleic acid), folic acid and its derivatives, ubiquinone and ubiquinol and their derivatives, Vitamin C and its derivatives (for example ascorbyl palmitate, magnesium ascorbyl phosphate, ascorbyl acetate), tocopherols and their derivatives (for example Vitamin E acetate), Vitamin A and its derivatives (for example Vitamin A palmitate) and also coniferyl benzoate of benzoin resin, rutinic acid and its derivatives, ferrulic acid and its derivatives, butylhydroxytoluene, butylhydroxyanisole, nordihydroguaiacic acid, nordihydroguaiaretic acid, trihydroxybutyrophenone, uric acid and its derivatives, mannose and its derivatives, zinc and its derivatives (for example ZnO, $ZnSO_4$), selenium and its derivatives (such as selenium methionine), stilbenes and their derivatives (such as stilbene oxide, trans-stilbene oxide), as well as the derivatives (such as salts, esters, ethers, sugars, nucleotides, nucleosides, peptides and lipids) of said active compounds such as are suitable in accordance with the invention.

The surfactant containing formulation, preferably a cosmetic or pharmaceutical formulation, according to the present invention can also contain one or more vitamins and vitamin precursors, wherein any vitamins and vitamin precursors which are suitable or customary in cosmetic or pharmaceutical applications can be used. Particular mention may be made here of vitamins and vitamin precursors such as tocopherols, Vitamin A, nicotinic acid and nicotinamide, other B-complex vitamins, in particular biotin, and Vitamin C. Other examples within this group which are preferably used include pantothenyl alcohol and its derivatives, in particular its esters and ethers, as well as derivatives of pantothenyl alcohols obtained cationically, such as for example pantothenyl alcohol triacetate, pantothenyl alcohol monoethyl ether and its monoacetate and also cationic pantothenyl alcohol derivatives.

The surfactant containing formulation, preferably a cosmetic or pharmaceutical formulation, according to the present invention can also contain one or more active compounds having a skin-lightening action, wherein any skin-lightening active compounds that are suitable or customary in cosmetic or pharmaceutical applications can be used in accordance with the invention. Advantageous skin-lightening active compounds in this regard include kojic acid, hydroquinone, arbutin, ascorbic acid, magnesium ascorbyl phosphate, resorcinols, liquorice root extracts and their constituents glabridin or licochalcone A, or extracts from *Rumex* and *Ramulus* species, extracts from pine species (*Pinus*) or extracts from *Vitis* species which contain inter alia skin-lightening stilbene derivatives.

The surfactant containing formulation, preferably a cosmetic or pharmaceutical formulation, according to the present invention can also contain mono-, di- and oligosaccharides such as for example glucose, galactose, fructose, mannose and lactose.

The surfactant containing formulation, preferably a cosmetic or pharmaceutical formulation, according to the present invention can also contain one or more plant extracts, which are usually prepared by extraction of the complete plant, but which in individual cases are also prepared exclusively from the blossom and/or leaves, wood, bark or roots of the plant. With regard to the plant extracts which can be used in accordance with the present invention, reference is made in particular to the extracts listed in the table starting on page 44 of the third edition of *Leitfaden zur Inhaltsstoffdeklaration kosmetischer Mittel* (Guide to the Declaration of Constituents of Cosmetic Agents), published by *Industrieverband Körperpflegemittel und Waschmittel* e. V. (IKW) (Industrial Association for Toiletries and Detergents), Frankfurt. Particularly advantageous extracts include aloe, *Hamamelis*, algae, oak bark, willow-herb, stinging nettles, dead nettles, hops, camomile, milfoil, *arnica, calendula*, burdock root, horse-tail, hawthorn, linden blossom, cucumber, almonds, pine needles, horse chestnut, sandalwood, juniper, coconut, mango, apricot, orange, lemon, lime, grapefruit, apple, green tea, grapefruit seed, wheat, oats, barley, sage, thyme, basil, rosemary, birch, mallow, bitter-crass, willow bark, restharrow, coltsfoot, *althaea, ginseng* and ginger root. Of these, particularly preferred extracts include aloe vera, camomile, algae, rosemary, *calendula, ginseng*, cucumber, sage, stinging nettles, linden blossom, *arnica* and *Hamamelis*. Mixtures of two or more plant extracts can also be employed. Extraction agents that can be used for preparing said plant extracts include water, alcohols and mixtures thereof. Preferred alcohols in this context are the lower alcohols such as ethanol and isopropanol, but also polyhydric alcohols such as ethylene glycol, propylene glycol and butylene glycol, specifically both as a sole extracting agent and in mixtures with water. The plant extracts can be used in pure form or dilute form in accordance with the invention.

The surfactant containing formulation, preferably a cosmetic or pharmaceutical formulation, according to the present invention may also include at least one further fragrance substance. The following specified fragrance substances can be used, either as individual substances or in mixtures with at least one, two, three or even more fragrance substances, in a large number of fragrance mixtures, selected from an extensive range of natural and synthetic substances.

Fragrance substances which are advantageously suitable for combining are listed for example in S. Arctander, Perfume and Flavor Materials, volumes I and II, Montclair, N.J. 1969, private publication, and/or in H. Surburg, J. Panten, Common Fragrance and Flavor Materials, $6^{th}$ edition, Wiley-VCH, Weinheim 2016. The following list comprises examples of known odourant substances:

- extracts of natural raw materials such as essential oils, concretes, absolutes, resins, resinoids, balsams, tinctures such as for example: ambergris tincture; *amyris* oil; *angelica* seed oil; *angelica* root oil; anise oil; valerian oil; basil oil; tree moss absolute; bay oil; *artemisia* oil; benzoin resin; bergamot oil; beeswax absolute; birch tar oil; bitter almond oil; savory oil; buchu leaf oil; cabreuva oil; cade oil; calamus oil; camphor oil; *cananga* oil; cardamom oil; cascarilla oil; *cassia* oil; cassie absolute; castoreum absolute cedar leaf oil; cedarwood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; *Eucalyptus citriodora* oil; *eucalyptus* oil; fennel oil; pine-needle oil; *galbanum* oil; *galbanum* resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; *Litsea cubeba* oil; bay leaf oil; mace oil; marjoram oil; mandarin oil; *massoia* bark oil; *mimosa* absolute; ambrette oil; musk tincture; muscatel sage oil; nutmeg oil; myrrh absolute; myrrh oil; myrtle oil; clove leaf oil; clove bud oil; neroli oil; olibanum absolute; olibanum oil; *opopanax* oil; orange blossom absolute; orange oil; *origanum* oil; palmarosa oil; patchouli oil; *perilla* oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike lavender oil; star anise oil; *styrax* oil; *tagetes* oil; fir needle oil; tea tree oil; terpentine oil; thyme oil; Tolu balsam; tonka absolute; tuberose absolute; vanilla extract; violet leaf absolute; *verbena* oil; vetiver oil; juniper berry oil; cognac oil; wormwood oil; wintergreen oil; ylang ylang oil; hyssop oil; civet absolute; cinnamon leaf oil; cinnamon bark oil, and fractions thereof or constituents isolated therefrom;
- individual fragrance substances from the group comprising hydrocarbons, such as for example 3-carene; alpha-pinene; beta-pinene; alpha-terpinene; gamma-terpinene; p-cymene; bisabolene; camphene; caryophyllene; cedrene; famesene; limonene; longifolene; myrcene; ocimene; valencene; (E,Z)-1,3,5-undecatriene; styrene; diphenylmethane;
- aliphatic alcohols such as for example hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixtures of 3,4,5,6,6-pentamethyl-3,4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;
- aliphatic aldehydes and the acetals thereof such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; 1-(1-methoxypropoxy)-(E/Z)-3-hexene;
- aliphatic ketones and the oximes thereof such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;
- aliphatic sulphur-containing compounds such as for example 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol; aliphatic nitriles such as for example 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;
- esters of aliphatic carboxylic acids such as for example (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate;

butyl butyrate; isoamyl butyrate; hexyl butyrate; (E)- and (Z)-3-hexenyl-isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl-crotonate;

acyclic terpene alcohols such as for example: citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

acyclic terpene aldehydes and ketones such as for example geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, 7-hydroxy-3,7-dimethyloctanal;

cyclic terpene alcohols such as for example: menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

cyclic terpene aldehydes and ketones such as for example menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedryl ketone);

cyclic alcohols such as for example: 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols such as for example alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers such as for example: cineole; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodeca-hydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones such as for example 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes such as for example 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones such as for example 1-(3,3-dimethyl-cyclohexyl)-4-penten-1-one; 2,2-dimethyl-1-(2,4-dimethyl-3-cyclohexene-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl-(2,4-dimethyl-3-cyclohexen-1-yl) ketone;

esters of cyclic alcohols such as for example 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a,4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate;

esters of cycloaliphatic alcohols such as for example 1-cyclohexylethyl crotonate; esters of cycloaliphatic carboxylic acids such as for example allyl-3-cyclohexyl propionate; allylcyclohexyl oxyacetate; cis- and trans-methyl dihydrojasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane 2-acetate;

araliphatic alcohols such as for example benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids such as for example benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenyl-ethyl butyrate; cinnamyl acetate; 2-phenoxyethyl isobutyrate; 4-methoxybenzyl acetate; araliphatic ethers such as for example: 2-phenyl ethyl methyl ether; 2-phenyl ethyl isoamyl ether; 2-phenyl ethyl 1-ethoxyethyl ether; phenylacetaldehyde dimethylacetal; phenylacetaldehyde diethylacetal; hydratropaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes such as for example: benzaldehyde; phenylacetaldehyde; 3-phenylpropanal; hydratropaldehyde; 4-methylbenz-aldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones such as for example: acetophenone; 4-methyl-acetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and the esters thereof such as for example: benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenyl glycidate; ethyl-3-methyl-3-phenyl glycidate;

nitrogenous aromatic compounds such as for example: 2,4,6-trinitro-1,3-dimethyl-5-tert-butylbenzene; 3,5-dinitro-2,6-dimethyl-4-tert-butyl aceto-phenone; cinnamonitrile; 3-methyl-5-phenyl-2-pentenoic acid nitrile; 3-methyl-5-phenylpentanoic acid nitrile; methyl anthranilate; methyl-N-methyl anthranilate; Schiff bases of methyl anthranilate with 7-hydroxy-3,7-dimethyloctanal, 2-methyl-3-(4-tert-butylphenyl)propanal or 2,4-dimethyl-3-cyclohexene carbaldehyde 6-isopropyl quinoline; 6-isobutyl quinoline; 6-sec-butyl quinoline; 2-(3-phenylpropyl)pyridine; indole; skatole; 2-methoxy-3-isopropylpyrazine; 2-isobutyl-3-methoxypyrazine;

phenols, phenyl ethers and phenyl esters such as for example: estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds such as for example: 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones such as for example: 1,4-octanolide; 3-methyl-1,4-octanolide; 1,4-nonanolide; 1,4-decanolide; 8-decen-1,4-olide; 1,4-undecanolide; 1,4-dodecan-olide; 1,5-decanolide; 1,5-dodecanolide; 4-methyl-1,4-decanolide; 1,15-penta-decanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin;

and mixtures of the above substances.

The surfactant containing formulation, preferably a cosmetic or pharmaceutical formulation, according to the present invention may also include a cosmetically or pharmaceutically acceptable carrier, such as (without being limited to) one of the following which are commonly used in the art: lactose, dextrose, sucrose, sorbitol, mannitol, starch, acacia rubber, calcium phosphate, alginate, gelatine, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil and the like. The cosmetic or pharmaceutical, in particular dermatological, formulation may also include lubricants, wetting agents, sweeteners, flavouring agents, emulsifiers, suspensions, preserving agents and the like, in addition to the above components. Suitable pharmaceutically acceptable carriers and preparations are described in detail in Remington's Pharmaceutical Sciences ($19^{th}$ edition, 1995).

The surfactant containing formulation, preferably a cosmetic or pharmaceutical formulation, according to the present invention may also contain one or more emulsifiers commonly used in the art for preparing a cosmetic or pharmaceutical formulation.

The surfactant containing formulation according to the present invention can be easily formulated as conventional cosmetic or pharmaceutical formulations for personal care, preferably for skin, hair, scalp and nail care.

In a further aspect the present invention therefore relates to cosmetic or pharmaceutical, preferably dermatological, surfactant containing formulations or preparations for personal care, preferably for skin, hair, scalp and nail care.

Within the context of the present invention, the surfactant containing formulation, preferably the cosmetic or pharmaceutical, in particular dermatological, formulation, according to the present invention can be provided either in liquid or solid form. Preferably, the formulations according to the present invention can take various forms such as are for example customarily employed for this type of formulations and suitable for topical application, for example as lotions, aqueous or aqueous-alcoholic gels, vesicle dispersions, liquids, semi-liquids or solids, such as milks, creams, gels, cream-gels, pastes or sticks, and can optionally be packaged as an aerosol and take the form of mousses or sprays. These formulations are prepared according to usual methods.

In a preferred variant, the cosmetic or pharmaceutical, in particular dermatological, surfactant containing formulations according to the present invention are selected from the group consisting of solid soap, liquid soap, cleansing products, cleansing gel, bath and shower additives, hair, skin and body shampoo, hair conditioner, shaving products, antidandruff shampoo and micellar water.

In a preferred variant of the present invention, the aforementioned products are either formulated as rinse-off products or as leave-on products. Rinse-off product means any substance, or mixture of substances, manufactured for the purpose of being applied to any relevant human body part in the course of any personal care treatment, by an application which entails at its completion the prompt and specific removal of the product (or any residue of the product) by washing or rinsing with water, rather than leaving it to wear off, or be absorbed or shed, in the course of time. By contrast, leave-on product means a cosmetic product that do not require rinse-off and which is intended to stay in prolonged contact with the skin, the hair, the scalp or the nails, for example conditioning formulations, usually applied after shampoo.

In a preferred variant of the present invention, the formulation comprising the surfactant containing formulation is a rinse-off shampoo or a leave-on conditioner.

In order to be used, the cosmetic or pharmaceutical, in particular dermatological, formulation according to the present invention is applied to the skin, hair, scalp and/or nails in an adequate amount in such manner as is customary with cosmetics and dermatological products.

The pseudoceramide compound used according to the present invention has a significantly better solubility in the surfactant containing formulation compared to Ceramide 2 or Ceramide 3. Additionally, said pseudoceramide compound does not precipitate in the surfactant containing formulation and, thus, does not lead to turbidity.

Thus, due to the better solubility of the pseudoceramide compound, a clear, non-turbid and stable surfactant containing formulation can be obtained and even maintained during storage.

Due to the better solubility, the pseudoceramide compound used according to the present invention is available in the surfactant containing formulation in a high concentration resulting in an improved bioavailability of the pseudoceramide compound.

Due to the better solubility of the pseudoceramide compound, the surfactant containing formulation according to the present invention advantageously goes without a lipophilic solvent, such as hexyldecanol, the addition of which to a surfactant containing formulation usually results in a breakdown of the surfactant containing formulation and, thus, leads to a turbid unstable solution with decreased viscosity.

Because of said distinguished properties, the surfactant containing formulation according to the present invention can be advantageously used for strengthening the barrier function of the skin, hair, scalp and nail, and, thus, can improve the water retention capacity of the stratum corneum, can help with a variety of skin and hair problems, such as reducing fine lines and wrinkles, can prevent dry skin and keep hair soft and nails healthy.

The treatment of hair with a shampoo formulation containing the pseudoceramide according to the present invention improves hair luster. A leave-on formulation containing the pseudoceramide according to the present invention, such as conditioner, increases hair fibers hydrophobicity.

The surfactant containing formulations according to the present invention are prepared by conventional methods known per se, e.g. by incorporating one or more of the following components to be used according to the present invention: (a) at least one surfactant, (b) at least one N-acyl-hydroxamino acid ester of the general formula (I), and (c) optionally at least one cosmetically and/or pharmaceutically, in particular dermatologically, active auxiliary substance and/or additive.

In a final aspect, the present invention relates to the use of at least one N-acyl-hydroxyamino acid ester of the general Formula (I)

Formula (I)

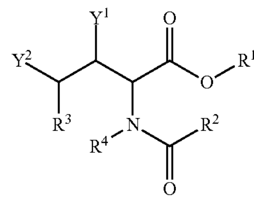

or an enantiomer thereof, as described and defined above, or the use of an N-acyl hydroxyamino acid ester as represented by the formula (II)

Formula (II)

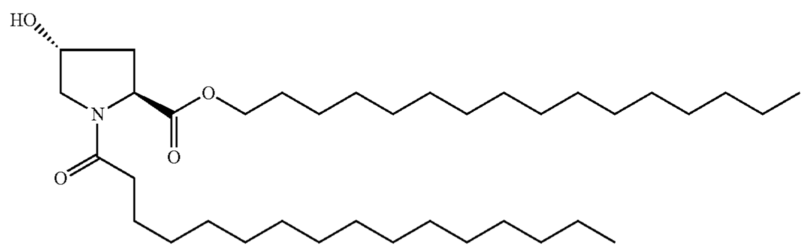

or an enantiomer thereof, for the preparation of a surfactant containing formulation.

The present invention shall now be described in detail with reference to the following examples, which are merely illustrative of the present invention, such that the content of the present invention is not limited by or to the following examples.

EXAMPLES

Example 1: Solubility

The solubility of the pseudoceramide CeramideBio in shampoo is evaluated in comparison to Ceramide 2 and Ceramide 3.

Shampoo Formulations:

Surfactant content: Approx. 14% 01

TABLE 1

| | Raw Material | INCI | 01_B | 02_B | 03_B |
|---|---|---|---|---|---|
| A | Plantacare PS10 ex BASF | Sodium laureth sulfate, lauryl glycoside | 17.0 | 17.0 | 17.0 |
| | Citric acid | Citric acid | 0.15 | 0.15 | 0.15 |
| | SymDiol ® 68 [108580] | 1,2-Hexanediol, caprylyl glycol | 1.0 | 1.0 | 1.0 |
| | EDTA BD ex BASF | Disodium EDTA | 0.1 | 0.1 | 0.1 |
| B | Water, demin. | Water (Auqa) | 74.0 | 74.0 | 74.0 |
| | Ucare Polymer JR-400 | Polyquaternium-10 | 0.2 | 0.2 | 0.2 |
| | CeramideBio according to the pesent invention | Cetylhydroxyproline palmitamide | 0.1 | — | — |
| | Ceramide 2 | Ceramide 2 | — | 0.1 | — |
| | Ceramide 3 | Ceramide 3 | — | — | 0.1 |
| | Tegosoft PC-41 ex Evonik | Polyglyceryl-4-caprate | 2.0 | 2.0 | 2.0 |
| C | Potassium sorbate | Potassium sorbate | 0.15 | 0.15 | 0.15 |
| D | Tego Betain F50 ex Evonik | Cocoamidoproyl betaine | 5.0 | 5.0 | 5.0 |
| E | Sodium chloride | Sodium chloride | 0.4 | 0.4 | 0.4 |
| | | Sum | | 100.0 | |
| | | pH value | | 5.6 | |

Production Method:

The shampoo formulations were prepared as follows:

Phase A components were blended by gentle stirring; the process was stopped, when foaming starts.

The ceramides/pseudoceramide were predispersed in polyglyceryl-4-caprate and heated up to 90° C. The ceramides/pseudoceramide were melted and finely dispersed. Ucare Polymer JR-400 and water were added and the mixture was heated up to 90° C. again and stirred for 10 minutes.

Phases B, C and D were added to phase A one after the other by stirring. After that, the mixture was stirred slowly with a vane stirrer until the solution was homogeneous. At last Phase E was added by stirring with a vane stirrer. The pH value was adjusted to about 5.4 to 5.8.

The visual appearance of the shampoo formulations was evaluated after preparation, after 3 days storage at 5° C. and 3 day at room temperature.

The visual appearance of the shampoo formulations is depicted in FIG. 1. From left to the right: Sample CeramideBio (01_B), Ceramide 2 (02_B), Ceramide 3 (03_B).

The shampoo formulation with CeramideBIO according to the present invention could be incorporated into shampoo without recrystallization whereas the shampoo formulations with Ceramide 2 and Ceramide 3 showed recrystallization.

Example 2: Foam Volume

The foam volume of the shampoo formulation as specified in Example 1 was measured.

Method:

200 ml of a solution of the shampoo formulations (1% shampoo in dem. water) were transferred into the foam volume and drainage measuring instrument (Ernst Haage). Then the stamp is pulled up and pushed down in constant intervals. The volume of the foam is recorded every 10 swings for 8 times.

TABLE 2

| | | Times | | | | | | | |
|---|---|---|---|---|---|---|---|---|---|
| | | 10 | 20 | 30 | 40 | 50 | 60 | 70 | 80 |
| Volume [ml] | 1. Measurement 01_B | 400 | 700 | 950 | 1200 | 1350 | 1500 | 1650 | 1750 |
| | 2. Measurement 01_B | 500 | 750 | 1050 | 1250 | 1350 | 1500 | 1600 | 1700 |
| | MW | 450 | 725 | 1000 | 1225 | 1350 | 1500 | 1625 | 1725 |
| | 1. Measurement 02_B | 250 | 600 | 800 | 1000 | 1150 | 1200 | 1300 | 1350 |
| | 2. Measurement 02_B | 300 | 750 | 900 | 1100 | 1250 | 1350 | 1450 | 1500 |
| | MW | 275 | 675 | 850 | 1050 | 1200 | 1275 | 1375 | 1425 |
| | 1. Measurement 03_B | 400 | 650 | 900 | 1150 | 1250 | 1400 | 1500 | 1650 |
| | 2. Measurement 03_B | 400 | 700 | 900 | 1050 | 1200 | 1350 | 1450 | 1600 |
| | MW | 400 | 675 | 900 | 1100 | 1225 | 1375 | 1475 | 1625 |

The foam volume with the shampoo formulation according to the present invention (CeramideBio; 01_B) was higher compared to the foam volume with the shampoo formulations with Ceramide 2 (02_B) and Ceramide 3 (03_B). The higher the foam volume is, the more cleansing efficiency has the formulation due to an increase of the active surface.

Example 3: Hair Shine/Luster

The hair luster was measured with a shampoo formulation according to the present invention containing pseudoceramide CeramideBio (shampoo, 1.0%), a shampoo formulation containing Ceramide 2 (shampoo, 1%) and a Placebo (shampoo).

Principle: Hair luster test analyzes the light reflection from the hair surface and other interactions of the incident light with the hair. The measurement is made by using SAMBA system. The results are expressed by luster: parameter calculated from values of shine, chroma and diffused light to express the observer perception of the gloss effect. The higher is the value, the best impression of the observer regarding gloss effect of the hair.

Luster Evaluation:

- 5 Caucasian hair tresses per group (5 g, 25 cm, 3× bleached) were cleaned with a sodium laureth sulfate solution (SLES) (10%) for 1 minute;
- The tresses were left for drying at controlled environment (22±2° C.; 50±5% relative humidity) overnight;
- Measurement in initial time (T0) was performed;
- Test samples (see above) were applied 5 times to each tress (0.5 ml of sample; massaging for 1 minute, followed by 1 minute of rinsing under running water (33±3° C.);
- Tresses were left for drying at controlled environment (22±2° C.; 50±5% RH) overnight;
- Measurement in final time (T1) was performed,
- Comparisons among treatments were performed using one-way variance analysis (ANOVA), followed by Tukey's honestly significant difference (HSD) test, at a 95% confidence interval.

Figure 2:
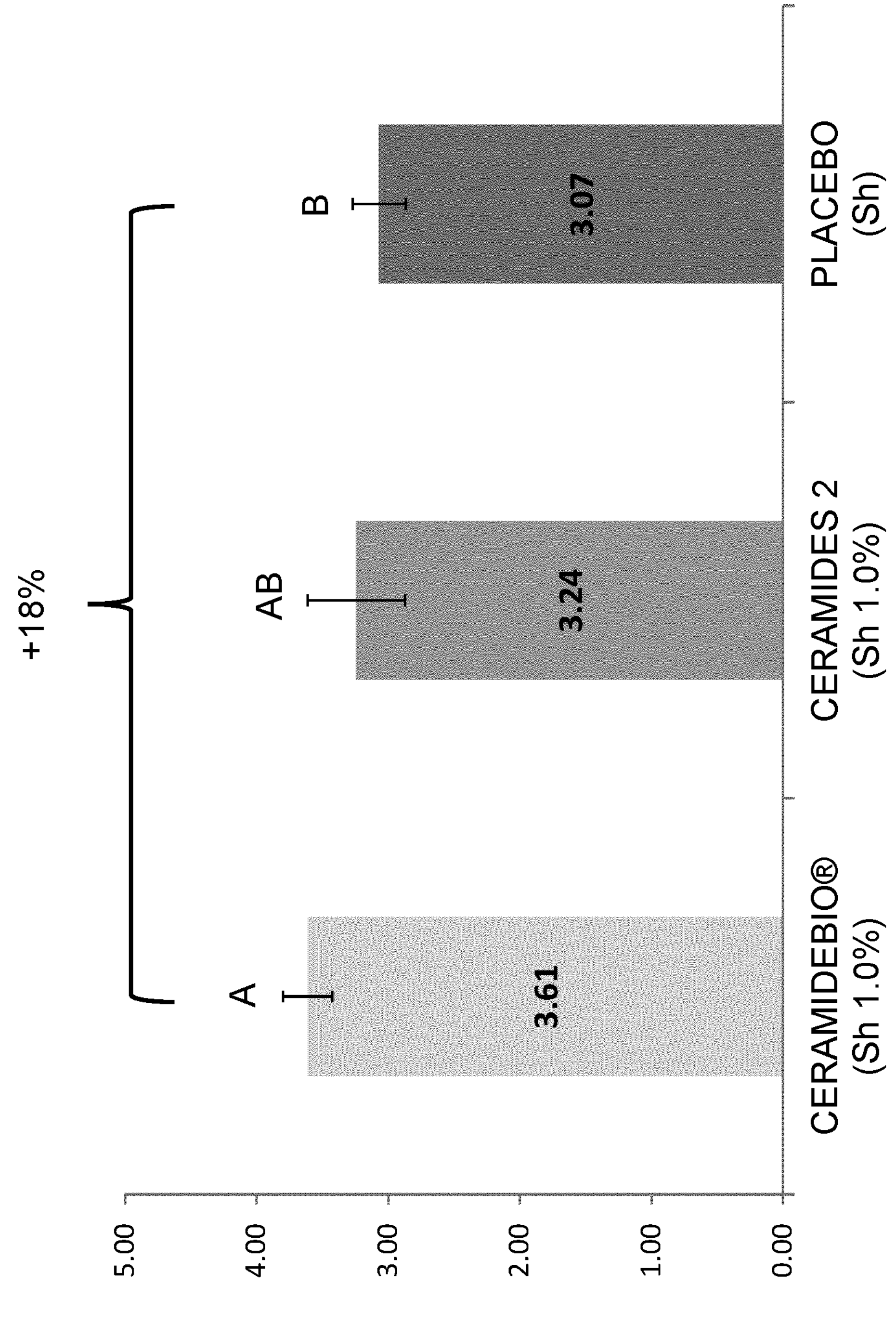
FIG. 2 is a diagram, depicting the results of a luster evaluation of hair after treatment with different shampoo formulations.

The results of the luster evaluation are represented in FIG. 2.

The luster of the hair after application of the shampoo formulation according to the present invention (CeramideBio) was higher compared to luster of the hair after application of the shampoo formulation with Ceramide 2.

The treatment with a shampoo formulation containing 1.0% of CeramideBio according to the present invention was able to increase hair luster.

Example 4: Swelling/Hydrophobicity

The swelling of the hair was measured with a conditioning formulation according to the present invention containing pseudoceramide CeramideBio (leave-on, 0.5 and 0.05%), a conditioning formulation containing Ceramide 2 (leave-on, 0.5% and 0.05%) and a Placebo (leave-on). Leave-on means a conditioning formulation, that do not require rinse-off.

Principle: Through diameter measurements it is possible to determine the level of swelling of a hair fiber over time when in contact with water. The swelling test evaluates the action of materials in forming a hydrophobic film on hair surface in order to prevent humidity from penetrating the hair, which in turn provokes the hair diameter variation. The laser measures the variation in the fiber diameter as it absorbs water over a pre-determined time. According to the fiber condition or the film covering its surface, the level of swelling may change. The more damaged the hair, the more hydrophilic it is, since most of the hair damages take the lipids, ceramides and other hydrophobic substances away from the hair, and, consequently, more swelling is noticed. Parameter measured: variation in hair diameter (%).

Swelling Test:

- 3 Caucasian hair tresses (2.5 g, 25 cm, 1× bleached) were cleaned with a sodium laureth sulfate solution (SLES) (10%) for 1 minute;
- Test samples (see above) were applied to each tress (0.25 ml of sample; massaging for 1 minute);
- Tresses were left for drying at controlled environment (22±2° C.; 50±5% RH) overnight;
- 45 fibers from each treatment were collected randomly and fixed in plastic tabs one by one;
- Swelling test was performed during 180 s;
- Variation on fiber's diameter was calculated;
- Comparisons among treatments were performed using one-way variance analysis (ANOVA), followed by Tukey's honestly significant difference (HSD) test, at a 95% confidence interval.

Figure 3:
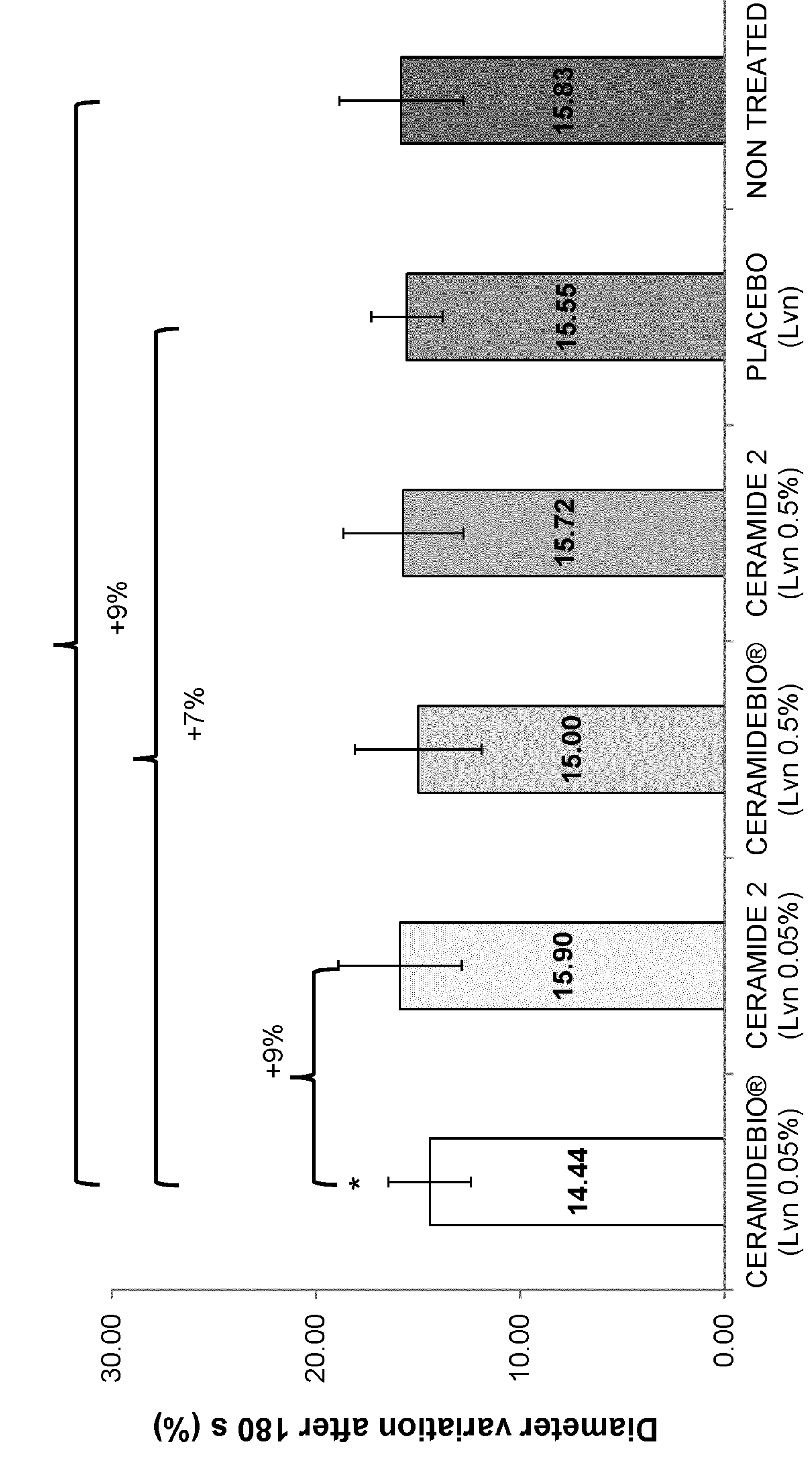
FIG. 3 is a diagram, depicting the results of a swelling test of hair fibers after treatment with different leave-on conditioning formulations.

The results of the swelling test are represented in FIG. 3.

The diameter variation of the hair after 180 s after application of the conditioning formulation according to the present invention (CeramideBio) was smaller compared to the diameter variation of the hair after 180 s after application of the conditioning formulation with Ceramide 2. The sample of CeramideBio in the lower concentration has a better diameter variation (14.44) than the CeramideBio in the higher concentration (15.90).

The treatment with the leave-on formulation containing 0.05% of CeramideBio according to the present invention was able to increase the hair fiber's hydrophobicity, statistically decreasing its swelling when compared to non-treated hair, to hair treated with placebo formulation and with leave-on formulation containing 0.05% of Ceramide 2. Thus, the treatment with CeramideBio returned to hair hydrophobicity, a characteristic of the virgin hair, which protects the hair from water penetration.

The invention claimed is:

1. A surfactant containing formulation, comprising (a) ≥5% by weight of at least one surfactant, based on the total weight of the formulation;

(b) at least one N-acyl-hydroxyamino acid ester of the general Formula (I)

Formula (I)

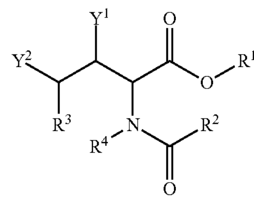

or an enantiomer thereof, wherein

R1 is a linear, branched or cyclic alkyl or alkenyl group having 5 to 50 carbon atoms and optionally substituted by one or more hydroxyl group(s), R2 is a linear or branched alkyl or alkenyl group having 1 to 49 carbon atoms and optionally substituted by one or more hydroxyl group(s), Y1 and Y2 are independently of one another, hydrogen or a hydroxyl group, R3 and R4 are either independently of one another, hydrogen or a linear or branched alkyl or alkenyl group having 1 to 10 carbon atoms, or R3 and R4 together are an alkyl group having 1 to 3 carbon atoms or together with the chain between R3 and R4 form a 5- to 7-membered heterocyclic ring, wherein the alkyl group is optionally substituted by 1 to 3 linear or branched alkyl or alkenyl group(s) or is substituted by 1 to 3 hydroxyl group(s); and (c) optionally at least one cosmetically and/or pharmaceutically active substance and/or additive.

2. Surfactant containing formulation according to claim 1, wherein in the general Formula (I) R1 and/or R2 are a linear or branched alkyl or alkenyl group having 10 to 20 carbon atoms, optionally substituted by 1 to 3 hydroxyl group(s).

3. Surfactant containing formulation according to claim 1, wherein in the general Formula (I) one of Y1 or Y2 is a hydroxyl group and the other is hydrogen.

4. Surfactant containing formulation according to claim 1, wherein in the general Formula (I) R3 and R4 independently of one another are hydrogen or a linear or branched alkyl or alkenyl group having 1, 2, 3 or 4 carbon atoms, or R3 and R4 together are $—CH_2—$, $—CH_2—CH_2—$, —CH(OH)—, $—CH(OH)—CH_2—$ or $CH_2—CH(OH)—$, in order to form a closed heterocyclic ring.

5. Surfactant containing formulation according to claim 1, wherein in the general Formula (I) either R3 and R4 each are hydrogen and Y1 and Y2 independently of one another each are hydrogen or a hydroxyl group, or R3 and R4 together are $—CH_2—$ or —CH(OH)— and together with the chain between R3 and R4 form a 5-membered heterocyclic ring und concurrently Y1 and Y2 independently of one another are hydrogen or a hydroxyl group.

6. Surfactant containing formulation according to claim 1, wherein in the general Formula (I) either R3 and R4 each are hydrogen and Y1 and Y2 independently of one another each are hydrogen or a hydroxyl group, or R3 and R4 together represent $—CH_2—$ and together with the chain between R3 and R4 form a 5-membered heterocyclic ring and one of the two Y1 and Y2 is a hydroxyl group.

7. Surfactant containing formulation according to claim 1, wherein in the general Formula (I) R1 is a linear alkyl group having 14 to 18 carbon atoms and R2 is a linear alkyl group having 13 to 18 carbon atoms.

8. Surfactant containing formulation according to claim 1, wherein the N-acylhydroxyamino acid ester is represented by the Formula (II):

Formula (II)

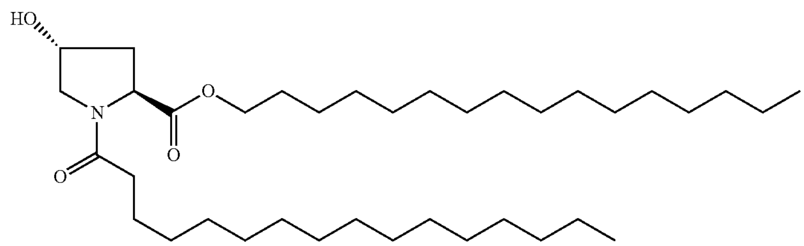

or an enantiomer thereof.

9. Surfactant containing formulation according to claim 1 comprising at least ≥7% by weight of at least one surfactant, based on the total weight of the formulation.

10. Surfactant containing formulation according to claim 1, wherein the at least one surfactant is selected from the group consisting of anionic, cationic, non-ionic and amphoteric or zwitterionic surfactants or a mixture thereof.

11. Surfactant containing formulation according to claim 1, wherein the anionic surfactant is selected from the group consisting of ammonium lauryl sulfate, ammonium laureth sulfate, sodium coco-sulfate, sodium laureth sulfate, sodium lauryl sarcosinate, sodium myreth sulfate, sodium pareth sulfate, sodium lauryl sulfate, TIPA-Laureth Sulfate, α olefin sulfonate, sodium cocoyl lactylate, sodium stearyl lactylate, sodium acyl glutamate, sodium/ammonium cocoyl isethionate, sodium lauroyl sarcosinate, sodium cocoyl sarcosinate, sodium methyl cocoyl taurate, -lauroyl lactylate, -caproyl lactylate, disodium cocoyl glutamate, sodium laureth-13 carboxylate, sodium PEG-6 cocamide carboxylate, sodium C12-C14 olefin sulphonate, sodium C14-C16 olefin sulphonate, sodium lauryl sulphoacetate sodium sulphosuccinate, disodium laureth sulphosuccinate, disodium lauryl sulphosuccinate, sodium myreth sulphate, sodium C12-C13 pareth sulphate, sodium, ammonium- and TEA lauryl sulphate, sodium lauroyl methyl isethionate, sodium lauroamphoacetate, cocamide MIPA sodium lauroyl methyl isethionate, sodium lauroamphoacetate, sodium xylene sulfonate, sodium hydrolyzed potato starch dodecenylsuccinate and a mixture of two or more of the afore-mentioned anionic surfactants; and/or the cationic surfactant is selected from the group consisting of benzyl dimethylstearyl ammonium chloride, cetrimonium chloride, trimethyl ammonium chloride or bromide, lauryl or cetyl pyridinium chloride, alkyl dimethyl amine oxides or alkyl aminoethyl dimethyl amine oxides, benzalkonium chloride, polyquaternium-6, polyquaternium-7, polyquaternium-10, polyquaternium-22, polyquaternium-37, cocamide MEA, guar hydroxypropyltrimonium chloride, TEA-dodecylbenzenesulfonate, and a mixture of two or more of the afore-mentioned cationic surfactants; and/or the non-ionic surfactant is selected from the group consisting of cocamide MEA, cocamide DEA, cocamide MIPA, lauryl glucoside, decyl glycoside coco glycoside, PEG-40 hydrogenated castor oil, trideceth-9, polysorbate-20, polysorbate-60, polysorbate-80, laureth-2, laureth-4, PEG-7 glyceryl cocoate, cetearyl glucoside, lauramide DEA, lauramide MEA, glycol distearate, PEG-200-hydrogenated glyceryl palmate, PEG-120 methyl glucose dioleate, sorbitan sesquicaprylate; and mixtures of two or more of the afore-mentioned non-ionic sufactants; and/or the amphoteric or zwitterionic surfactant is selected from the group consisting of acyl/dialkyl ethylene diamine, for example sodium acyl amphoacetate, disodium acyl amphodipropionate, disodium alkyl amphodiacetate, sodium acyl amphohydroxypropyl sulphonate, disodium acyl amphodiacetate and sodium acyl amphopropionate; N-alkyl amino acids, for example aminopropyl alkyl glutamide, alkyl aminopropionic acid, sodium alkyl imidodipropionate, lauroamphocarboxyglycinate, or mixtures of two or more of the afore-mentioned amphoteric surfactants.

12. Surfactant containing formulation according to claim 1, further comprising (alpha-)bisabolol and/or phytosterol.

13. Surfactant containing formulation according to claim 1, wherein the cosmetically and/or pharmaceutically active substances and/or additives are selected from the group consisting of anti-inflammatories, antibacterial or antimycotic substances, substances having a reddening-alleviating or itch-alleviating action, lenitive substances, moisturisers and/or cooling agents, osmolytes, keratolytic substances, nurturing substances, anti-inflammatory, antibacterial or antimycotic substances, substances having a reddening-alleviating or itch-alleviating action, lenitive substances, antidandruff substances, or other active compounds such as solvents, fragrances antioxidants, preservatives, (metal) chelating agents, penetration enhancers, and/or cosmetically or pharmaceutically acceptable excipients.

14. A formulation for personal care comprising the surfactant containing formulation according to claim 1.

15. The formulation according to claim 14, where in the formulation is a solid soap, liquid soap, cleansing products, cleansing gel, bath or shower additives, hair, skin or body shampoo, hair conditioner, shaving products, antidandruff shampoo or micellar water.

16. A method for strengthening the barrier function of the skin, hair, scalp or nails comprising applying the surfactant containing formulation according to claim 1 to the skin, hair, scalp or nails.

17. A method for preparing a surfactant containing formulation comprising incorporating into the formulation at least one N-acyl-hydroxyamino acid ester of the general Formula (I)

Formula (I)

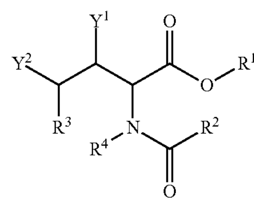

or an enantiomer thereof according to claim 1, or an N-acyl hydroxyamino acid ester as represented by the formula (II)

Formula (II)

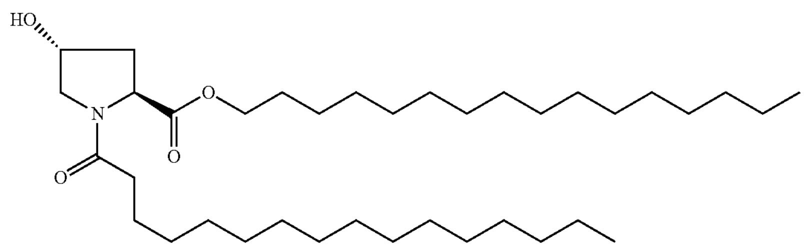

or an enantiomer thereof.

18. Surfactant containing formulation according to claim 1, wherein R1 is a linear, branched, or cyclic alkyl or alkenyl group having 5 to 24 carbon atoms and optionally substituted by 1 to 6 hydroxyl group(s).

19. Surfactant containing formulation according to claim 1, wherein R2 is a linear or branched alkyl or alkenyl group having 2 to 23 carbon atoms and optionally substituted by 1 to 6 hydroxyl group(s).

20. Surfactant containing formulation according to claim 2, wherein in the general Formula (I) one of Y1 or Y2 is a hydroxyl group and the other is hydrogen.

* * * * *